(12) United States Patent
Messersmith et al.

(10) Patent No.: US 9,687,582 B2
(45) Date of Patent: Jun. 27, 2017

(54) NEGATIVE-SWELLING AND EXCEPTIONALLY ROBUST ADHESIVE HYDROGELS

(71) Applicant: Northwestern University, Evanston, IL (US)

(72) Inventors: Phillip B. Messersmith, Clarendon Hills, IL (US); Devin G. Barrett, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/056,281

(22) Filed: Oct. 17, 2013

(65) Prior Publication Data
US 2014/0113989 A1    Apr. 24, 2014

Related U.S. Application Data

(60) Provisional application No. 61/715,403, filed on Oct. 18, 2012.

(51) Int. Cl.
| | | |
|---|---|---|
| *A61L 24/04* | (2006.01) | |
| *A61L 24/00* | (2006.01) | |
| *C08G 65/324* | (2006.01) | |
| *C08G 65/331* | (2006.01) | |
| *C08G 65/332* | (2006.01) | |
| *C08G 65/333* | (2006.01) | |
| *C08K 3/20* | (2006.01) | |

(52) U.S. Cl.
CPC ......... *A61L 24/046* (2013.01); *A61L 24/0031* (2013.01); *C08G 65/324* (2013.01); *C08G 65/332* (2013.01); *C08G 65/3317* (2013.01); *C08G 65/3332* (2013.01); *C08G 65/33303* (2013.01); *C08G 65/33306* (2013.01); *C08K 3/20* (2013.01); *C08G 2210/00* (2013.01); *C08G 2650/30* (2013.01)

(58) Field of Classification Search
USPC .................. 523/118, 177; 528/200
See application file for complete search history.

(56) References Cited

U.S. PATENT DOCUMENTS

| | | | |
|---|---|---|---|
| 6,440,366 B1 * | 8/2002 | Salpekar et al. ............. | 422/40 |
| 8,119,742 B2 * | 2/2012 | Dalsin et al. ............. | 525/408 |
| 2003/0087338 A1 * | 5/2003 | Messersmith et al. ...... | 435/68.1 |
| 2012/0116424 A1 * | 5/2012 | Lee ................. | A61L 24/046 606/151 |

OTHER PUBLICATIONS

Abdurrahmanoglu, et al., Design of High-Toughness Polyacrylamide Hydrogels by Hydrophobic Modification, Polymer, 2009, 50:5449-5455.
Achneck, et al., A Comprehensive Review of Topical Hemostatic Agents, Annals of Surgery, 2010, 251(2):217-228.
Alexandridis, et al., Micellization of Poly(ethylene oxide)-Poly(propylene oxide)-Poly(ethylene oxide) Triblock Copolymers in Aqueous Solutions: Thermodynamics of Copolymer Association, Macromolecules, 1994, 27(9):2414-2425.
Alexandridis, et al., Poly(ethylene oxide)-Poly(propylene oxide)-Poly(ethylene oxide) Block Copolymer Surfactants in Aqueous Solutions and at Interfaces: Thermodynamics, Structure, Dynamics, and Modeling, Colloids and Surfaces A: Physicochemical and Engineering Aspects, 1995, 96:1-46.
Allen, et al., Prospective Randomized Study Evaluating a Biodegradable Polymeric Sealant for Sealing Intraoperative Air Leaks that Occur During Pulmonary Resection, Ann. Thorac. Surg., 2004, 77:1792-1801.
Alvarez-Lorenzo, et al., Tetronic Micellization, Gelation and Drug Solubilization: Influence of pH and Ionic Strength, European Journal of Pharmaceutics and Biopharmaceutics, 2007, 66(2):244-252.
Anderson, et al., The Contribution of DOPA to Substrate-Peptide Adhesion and Internal Cohesion of Mussel-Inspired Synthetic Peptide Films, Adv. Funct. Mater., 2010, 20(23):4196-4205.
Artzi, et al., Characterization of Star Adhesive Sealants Based on PEG/Dextran Hydrogels, Macromolecular Bioscience, 2009, 9(8):754-765.
Azadani, et al., Mechanical Properties of Surgical Glues Used in Aortic Root Replacement, Ann. Thorac. Surg., 2009, 87:1154-1160.
Bilic, et al., Injectible Candidate Sealants for Fetal Membrane Repair: Bonding and Toxicity In Vitro, Am. J. Obstet. Gynecol., 2010, 202(1):85.e1-85.e9.
Blackburn, et al., Hydrogel-Induced Cervicomedullary Compression After Posterior Fossa Decompression for Chiari Malformation Case Report, Journal of Neurosurgery (4 Suppl Pediatrics), 2007, 106(4):302-304.
Brubaker, et al., Biological Performance of Mussel-Inspired Adhesive in Extrahepatic Islet Transplantation, Biomaterials, 2010, 31(3):420-427.
Brubaker, et al., Enzymatically Degradable Mussel-Inspired Adhesive Hydrogel, Biomacromolecules, 2011, 12:4326-4334.
Burke, et al., Thermal Gelation and Tissue Adhesion of Biomimetic Hydrogels, Biomed. Mater., 2007, 2:203-210.
Burzio, et al., Cross-Linking in Adhesive Quinoproteins: Studies with Model Decapeptides, Biochemistry, 2000, 39:11147-11153.
Cellesi, et al., Towards a Fully-Synthetic Substitute of Alginate: Development of a New Process Using Thermal Gelation and Chemical Cross-Linking, Biomaterials, 2004, 25(21):5115-5124.
Cellesi, et al., Materials for Cell Encapsulation Via a New Tandem Approach Combining Reverse Thermal Gelation and Covalent Crosslinking, Macromolecular Chemistry and Physics, 2002, 203(10-11):1466-1472.
Chiappetta, et al., Synergistic Encapsulation of the Anti-HIV Agent Efavirenz Within Mixed PoloxaminelPoloxamer Polymeric Micelles, Nanomedicine: Nanotechnology, Biology and Medicine, 2011, 7(5):624-637.

(Continued)

*Primary Examiner* — Tae H Yoon
(74) *Attorney, Agent, or Firm* — Quarles & Brady, LLP

(57) ABSTRACT

The present invention provides adhesive hydrogels that negatively swell at physiological temperature. By combining mussel-mimetic chemistry and the thermosensitive nature of poly(ethylene oxide)-poly(propylene oxide) copolymers, novel materials were designed that are suitable as medical sealants and adhesives.

18 Claims, 14 Drawing Sheets
(14 of 14 Drawing Sheet(s) Filed in Color)

(56) References Cited

OTHER PUBLICATIONS

Cho, et al., Formulation and Characterization of Poloxamine-Based Hydrogels as Tissue Sealants, Acta Biomaterialia, 2012, 8:2223-2232.

Cosgrove, et al., Safety and Efficacy of a Novel Polyethylene Glycol Hydrogel Sealant for Watertight Dual Repair, Journal of Neurosurgery, 2007, 106(1):52-58.

Fantner, et al. Sacrificial Bonds and Hidden Length: Unraveling Molecular Mesostructures in Tough Materials, Biophysical Journal, 2006, 90:1411-1418.

Garty, et al., Peptide-Modified "Smart" Hydrogels and Genetically Engineered Stem Cells for Skeletal Tissue Engineering, Biomacromolecules, 2010, 11(6):1516-1526.

Glickman, et al., A Polymeric Sealant Inhibits Anastomotic Suture Hole Bleeding More Rapidly Than Gelfoam/Thrombin, Results of a Randomized Controlled Trial, Arch. Surg., 2002, 137(3):326-331.

Go, et al., Tetronic-Oligolactide-Heparin Hydrogel as a Multi-Functional Scaffold for Tissue Regeneration, Macromolecular Bioscience, 2008, 8(12):1152-1160.

Haller, et al., Mussel-mimetic Tissue Adhesive for Fetal Membrane Repair: A Standardized Ex Vivo Evaluation Using Elastomeric Membranes, Prenatal Diagnosis, 2011, 31:654-660.

Hayes, et al., Viscoelastic Properties of Human Articular Cartilage, Journal of Applied Physiology, 1971, 31(4):562-568.

Holten-Andersen, et al., pH-induced Metal-Ligand Cross-Links Inspired by Mussel Yield Self-Healing Polymer Networks with Near-Covalent Elastic Moduli, PNAS, 2011, 108(7):2651-2655.

Huang, et al., Synthesis and Characterization of Self-Assembling Block Copolymers Containing Bioadhesive End Groups, Biomacromolecules, 2002, 3:397-406.

Jackson, Fibrin Sealants in Surgical Practice: An Overview, The American Journal of Surgery, 2001, 182:1S-7S.

Joch, The Safety of Fibrin Sealants, Cardiovascular Surgery, 2003, 11(Suppl 1):23-28.

Johnson, et al., Tensile and Viscoelastic Properties of Human Patellar Tendon, Journal of Orthopaedic Research, 1994, 12(6):796-803.

Kim, et al., Hydrogels: Swelling, Drug Loading, and Release, Pharmaceutical Research, 1992, 9(3):283-290.

Kjaergard, Suture Support: Is It Advantageous?, The American Journal of Surgery, 2001, 182(2)(Suppl 1):15S-20S.

Kjellander, et al., Water Structure and Changes in Thermal Stability of the System Poly(ethylene oxide)-Water, Journal of the Chemical Society, Faraday Transactions 1, 1981, 77:2053-2077.

Klimo, et al., Wound Complications Associated with the Use of Bovine Serum Albumin-Glutaraldehyde Surgical Adhesive in Pediatric Patients, Neurosurgery, 2007, 60(ONS Suppl 2):ONS-305-ONS-309.

Lau, Fibrin Sealant Versus Mechanical Stapling for Mesh Fixation During Endoscopic Extraperitoneal Inguinal Hernioplasty, Annals of Surgery, 2005, 242(5):670-675.

Lee, B., et al., Synthesis and Gelation of DOPA-Modified Poly(ethylene glycol) Hydrogels, Biomacromolecules, 2002, 3:1038-1047.

Lee, B., et al., Mussel-Inspired Adhesives and Coatings, Annu. Rev. Mater. Res., 2011, 41:99-132.

Lee, Y., et al., Thermo-Sensitive, Injectable, and Tissue Adhesive Sol-Gel Transition Hyaluronic Acid/Pluronic Composite Hydrogels Prepared from Bio-Inspired Catechol-thiol Reaction, Soft Matter, 2010, 6:977-983.

Leggat, et al., Surgical Applications of Cyanoacrylate Adhesives: A Review of Toxicity, ANZ J. Surg., 2007, 77:209-213.

Lv, et al., Designed Biomaterials to Mimic the Mechanical Properties of Muscles, Nature, 2010, 465:69-73.

Mak, The Apparent Viscoelastic Behavior of Articular Cartilage—The Contributions from the Intrinsic Matrix Viscoelasticity and Interstitial Fluid Flows, Journal of Biomechanical Engineering, 1986, 108(2):123-130.

Malcolm, et al., The Thermodynamic Properties of Aqueous Solutions of Polyethylene Glycol, Polypropylene Glycol and Dioxane, Transactions of the Faraday Society, 1957, 53:921-931.

Matsuda, et al., Fluorinated Water-Swollen Hydrogels with Molecular and Supramolecular Organization, Macromolecules, 2000, 33(7):2535-2538.

Mattamal, US FDA Perspective on the Regulations of Medical-Grade Polymers: Cyanoacrylate Polymer Medical Device Tissue Adhesives, Expert Review of Medical Devices, 2008, 5(1):41-49.

Mehdizadeh, et al., Injectable Citrate-Based Mussel-Inspired Tissue Bioadhesives with High Wet Strength for Sutureless Wound Closure, Biomaterials, 2012, 33:7972-7983.

Mulder, et al., Cauda Equina Compression by Hydrogel Dural Sealant After a Laminotomy and Discectomy: Case Report: Spine, 2009, 34(4):E144-E148.

Napoleone, et al., An Observational Study of CoSeal for the Prevention of Adhesions in Pediatric Cardiac Surgery, Interactive CardioVascular and Thoracic Surgery, 2009, 9:978-982.

Papov, et al, Hydroxyarginine-Containing Polyphenolic Proteins in the Adhesive Plaques of the Marine Mussel Mytilus Edulis, Journal of Biological Chemistry, 1995, 270(34):20183-20192.

Park, E., et al., Evaluation of Polyethylene Glycol Based Hydrogel for Tissue Sealing After Laparoscopic Partial Nephrectomy in a Porcine Model, Journal of Urology, 2004, 172(6)(Part 1):2446-2450.

Park, K., et al., (P 158) Enzyme-Triggered Injectable Hydrogel of Tetronic-Tyramine Conjugates for Tissue Regeneration, Tissue Engineering: Part A, 2008, 14(5):849.

Park, K., et al., In Situ Forming Hydrogels Based on Tyramine Conjugated 4-Arm-PPO-PEO Via Enzymatic Oxidative Reaction, Biomacromolecules, 2010, 11(3):706-712.

Park, K., et al., In Situ Hydrogelation and RGD Conjugation of Tyramine-Conjugated 4-Arm PPO-PEO Block Copolymer for Injectable Bio-Mimetic Scaffolds, Soft Matter, 2011, 7:986-992.

Park, K., et al., Synthesis and Characterizations of In Situ Cross-Linkable Gelatin and 4-Arm-PPO-PEO Hybrid Hydrogels Via Enzymatic Reaction for Tissue Regenerative Medicine, Biomacromolecules, 2012, 13(3):604-611.

Peng, et al., Novel Wound Sealants: Biomaterials and Applications, Expert Review of Medical Devices, 2010, 7(5):639-659.

Peppas, et al., Hydrogels in Biology and Medicine: From Molecular Principles to Bionanotechnology, Advanced Materials, 2006, 18:1345-1360.

Ranger, et al., Pneumostasis of Experimental Air Leaks with a New Photopolymerized Synthetic Tissue Sealant, American Surgeon, 1997, 63:788-795.

Ryou, et al., Tissue Adhesives: A Review, Techniques in Gastrointestinal Endoscopy, 2006, 8(1):33-37.

Ryu, et al., Catechol-Funtionalized ChitosanlPluronic Hydrogels for Tissue Adhesives and Hemostatic Materials, Biomacromolecules, 2011, 12(7):2653-2659.

Saeki, et al., Upper and Lower Critical Solution Temperatures in Poly(ethylene glycol) Solutions, Polymer, 1976, 17(8):685-689.

Sandell, et al., Correlation Between the Temperature Dependence of Apparent Specific Volume and the Conformation of Oligomeric Propylene Glycols in Aqueous Solution, Journal of Polymer Science Part A-2, 1971, 9(1):115-126.

Schmolka, et al., A Review of Block Polymer Surfactants, Journal of the American Oil Chemists' Society, 1977, 54(3):110-116.

Schwab, et al., Less Chronic Pain Following Mesh Fixation Using a Fibrin Sealant in TEP Inguinal Hernia Repair, Hernia, 2006, 10(3):272-277.

Seyednejad, et al., Topical Haemostatic Agents, British Journal of Surgery, 2008, 95:1197-1225.

Sosnik, et al., Poloxamine Hydrogels with a Quaternary Ammonium Modification to Improve Cell Attachment, Journal of Biomedical Materials Research Part A, 2005, 75a(2):295-307.

Sosnik, et al., Surface Study of Collagen/Poloxamine Hydrogels by a 'Deep Freezing' ToF-SIMS Approach, Biomaterials, 2006, 27(11):2340-2348.

Strehin, et al., A Versatile pH Sensitive Chondroitin Sulfate-PEG Tissue Adhesive and Hydrogel, Biomaterials, 2010, 31(10):2788-2797.

(56) References Cited

OTHER PUBLICATIONS

Taylor, et al., Viscoelastic Properties of Muscle-Tendon Units, The Biomechanical Effects of Stretching, American Journal of Sports Medicine, 1990, 18(3):300-309.

Than, et al., Polyethylene Glycol Hydrogel Dural Sealant May Reduce Incisional Cerebrospinal Fluid Leak After Posterior Fossa Surgery, Neurosurgery, 2008, 63(ONS Suppl 1):ONS-182-ONS-187.

Thavarajah, et al., Postoperative Cervical Cord Compression Induced by Hydrogel (DuraSeal): A Possible Complication, Spine, 2010, 35(1):E25-E26.

Ufret, et al., Evaluation of a Polyethylene Glycol (PEG)-Derived Glue as a Potential Bioadhesive for Vitreoretinal Applications, Investigative Ophthalmology & Visual Science, 2004, 45(Suppl 1):U767, E-Abstract 2054.

Waite, Evidence for a Repeating 3,4-Dihydroxyphenylalanine- and Hydroxyproline-Containing Decapeptide in the Adhesive Protein of the Mussel, *Mytilus edulis* L., Journal of Biological Chemistry, 1983, 258(5):2911-2915.

Waite, Nature's Underwater Adhesive Specialist, Int. J. Adhesion and Adhesives, 1987, 7(1):9-14.

Waite, et al., Polyphenolic Substance of *Mytilus edulis*: Novel Adhesive Containing L-DOPA and Hydroxyproline, Science, 1981, 212:1038-1040.

Waite, et al., Polyphosphoprotein from the Adhesive Pads of *Mytilus edulis*, Biochemistry, 2001, 40:2887-2893.

Wanka, et al., Phase Diagrams and Aggregation Behavior of Poly(oxyethylene)-Poly(oxypropylene)-Poly(oxyethylene) Triblock Copolymers in Aqueous Solutions, Macromolecules, 1994, 27(15):4145-4159.

Xu, et al., Synthesis and Micellization Properties of Double Hydrophilic A2BA2 and A4BA4 Non-Linear Block Copolymers, Macromolecules, 2006, 39:8178-8185.

You, et al., A Functionalizable Polyester with Free Hydroxyl Groups and Tunable Physiochemical and Biological Properties, Biomaterials, 2010, 31(12):3129-3138.

Yu, et al., Role of L-3,4-Dihydroxyphenylalanine in Mussel Adhesive Proteins, J. Am. Chem. Soc., 1999, 121:5825-5826.

Zhang, et al., A Novel Single Precursor-Based Biodegradable Hydrogel with Enhanced Mechanical Properties, Soft Matter, 2009, 5:3831-3834.

ASTM F2255-05, Standard Test Method of Strength Properties of Tissue Adhesives in Lap-Shear by Tension Loading, Book of Standards vol. 13.01, 2010, 2 pages.

\* cited by examiner

NEGATIVE-SWELLING AND EXCEPTIONALLY ROBUST ADHESIVE HYDROGELS

CROSS-REFERENCE TO RELATED APPLICATIONS

This application claims priority to U.S. Provisional Application No. 61/715,403 filed Oct. 18, 2012, the entirety of which is hereby incorporated by reference herein for all purposes.

STATEMENT REGARDING FEDERALLY SPONSORED RESEARCH

This invention was made with government support under grant number R37 DE014193 awarded by the National Institutes of Health. The government has certain rights in the invention.

FIELD OF THE INVENTION

This invention is directed to the synthesis and characterization of mechanically tough zero- or negative-swelling mussel-inspired surgical adhesives based on catechol-modified amphiphilic poly(propylene oxide)-poly(ethylene oxide) block copolymers.

BACKGROUND OF THE INVENTION

There is a growing need for new concepts in surgical wound closure due to limitations associated with invasive surgical closure techniques such as sutures and staples.[1-3] Medical adhesives and sealants that form in situ, many of which are approved for human clinical use, offer less invasive alternatives to conventional surgical closure techniques.[4-6] Several medical sealants are based on native proteins, for example fibrin glue and chemically cross-linked albumin.[4-7] While protein-based gels currently enjoy widespread use, their limitations include the possibility for disease transmission, allergic reactions, and poor mechanical properties.[6,8,9] As a result of these shortcomings, several synthetic surgical adhesives have been developed, including cyanoacrylates and hydrogels based on polymers such as poly(ethylene oxide) (PEO).[10-20] Cyanoacrylates exhibit excellent mechanical performance but their widespread use for internal procedures is limited by toxicity concerns.[10-12] PEO-based hydrogels, such as FocalSeal®, CoSeal®, and DuraSeal®, have satisfactory mechanical performance, are non-immunogenic, and have been used in cardiovascular,[13,14] pulmonary,[15,16] and dural[17,18] surgical procedures, among others.[19,20]

Swelling due to water absorption is a general feature of chemically cross-linked hydrophilic polymer networks.[21] The equilibrium swelling behavior of a polymer hydrogel is a reflection of the polymer-solvent interaction parameter, polymer architecture, extent of cross-linking, and polymer volume fraction.[22] In the context of in-situ forming medical adhesives, rapid covalent cross-linking of an aqueous polymer solution generally yields polymer hydrogels that are prone to significant swelling upon immersion into excess water.[2, 24] For PEO-based medical adhesives, observed swelling values range from 30% to >700%.[23,25,26] The consequences of swelling on the mechanical performance of tissue adhesives are underappreciated in the literature, as standard adhesion test methods often probe adhesion strength under non-equilibrium swelling conditions.[27] Swelling of medical adhesives and sealants in the minutes and hours following deployment in vivo can lead to severe medical complications such as local nerve compression.[28-30]

One possible approach to preventing swelling of polymer hydrogel tissue adhesives is to employ thermosensitive polymers.[31-35] Block copolymers of PPO and PEO, including commercially available multi-arm block copolymers composed of central PPO blocks and peripheral PEO blocks (Tetronic®), exhibit interesting thermosensitive behavior due to the hydrophilic-to-hydrophobic transition of the PPO block that occurs by mild warming.[31-34] Previous reports of chemically cross-linked Tetronic® hydrogels for cell encapsulation and tissue adhesion have appeared in the literature,[31,36-44] though systematic studies of the relationship between chemical cross-linking, thermal transition, and mechanical properties in the context of medical adhesion have not been undertaken.

BRIEF SUMMARY OF THE INVENTION

Herein, we describe the synthesis and characterization of in-situ forming polymer hydrogels with controllable swelling, good adhesion to soft tissue, and high mechanical robustness. Polymer gels were based on a branched amphiphilic PPO-PEO block copolymer terminated with catechols. The terminal catechol groups serve both an adhesive (interfacial) and cohesive (cross-linking) function, as they do in mussel adhesive proteins. This strategy has been employed in other mussel-mimetic adhesive hydrogels based on catechol-modified PEO, which have been evaluated in numerous in vitro, in vivo, and ex vivo studies.[25,26,45-48] Covalently cross-linked hydrogels were characterized by swelling, rheological, bulk compressive, and adhesive studies. These hydrogels exhibited controlled swelling and improved mechanical properties compared to similar PEO-based systems. Negative swelling systems with high mechanical toughness resulted from rapid chemical cross-linking followed by thermal equilibration, and a conceptual model is proposed for understanding the role of network structure in the observed mechanical properties.

Specifically, the present invention provides a method for making a non-swelling medical adhesive. The method comprises (a) contacting a composition comprising a catechol-modified poly(ethylene oxide)-poly(propylene oxide) block copolymer with a biocompatible oxidant at room temperature or below, whereby the catechol-modified poly(ethylene oxide)-poly(propylene oxide) block copolymer is chemically cross-linked to form a hydrogel; (b) increasing the temperature of the resulting hydrogel to physiological temperature; and (c) thermally equilibrating the hydrogel at physiological temperature, whereby the hydrogel exhibits no or negative swelling in an aqueous environment.

In one embodiment, the room temperature is about 20° C. or about 22° C. and physiological temperature is about 37° C.

In one embodiment, one or more terminal ends of the catechol-modified poly(ethylene oxide)-poly(propylene oxide) block copolymer includes a catechol moiety.

In one embodiment, the catechol-modified poly(ethylene oxide)-poly(propylene oxide) block copolymer has the structure $A(B-C)_4$, wherein A is

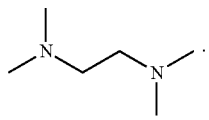

B is

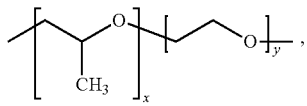

and

C is a catechol-terminating moiety.

In one embodiment,

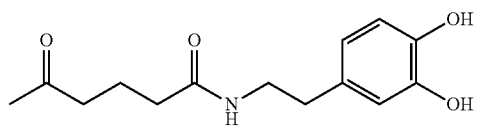 [SMILES: CC(=O)CCCC(=O)NCCc1ccc(O)c(O)c1]

C is.

In one embodiment, x and y are selected such that the poly(polyproylene oxide) is about 70% by weight of moiety B, and the poly(ethylene oxide) is about 30% by weight of moiety B.

In one embodiment, x and y are further selected such that the molecular weight of $A(B)_4$ is about 15 kDa and x is about 19.

In one embodiment, the oxidant is a periodate, such as but not limited to sodium periodate.

In one embodiment, the mole ratio of catechol present in the catechol-modified poly(ethylene oxide)-poly(propylene oxide) block copolymer to the periodate oxidant is 2:1.

The invention also provides a non-swelling medical adhesive made by the method described above.

The invention also provides a non-swelling medical adhesive comprising a hydrogel comprising two or more catechol-modified poly(ethylene oxide)-poly(propylene oxide) block copolymer molecules that are chemically cross-linked to each other between the catechol moieties of adjacent block copolymer molecules, wherein the hydrogel exhibits no or negative swelling in an aqueous environment.

In one embodiment, one or more terminal ends of the block copolymer molecules include a catechol moiety.

In one embodiment, the catechol-modified poly(ethylene oxide)-poly(propylene oxide) block copolymer molecules have the structure $A(B-C)_4$, wherein A is

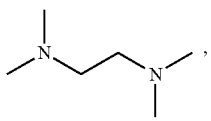

B is

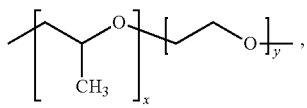

and

C is a catechol-terminating moiety.

In one embodiment,

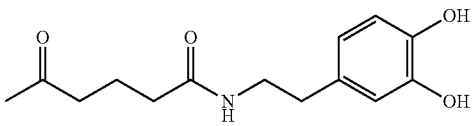 [SMILES: CC(=O)CCCC(=O)NCCc1ccc(O)c(O)c1]

C is.

In one embodiment, x and y are selected such that the poly(polyproylene oxide) is about 70% by weight of the block copolymer of B, and the poly(ethylene oxide) is about 30% by weight of the block copolymer of B.

In one embodiment, x and y are further selected such that the molecular weight of $A(B)_4$ is about 15 kDa.

In one embodiment, x is about 19.

DESCRIPTION OF THE DRAWINGS

The patent or application file contains at least one drawing in color. Copies of this patent or patent application publication with color drawings will be provided by the Office upon request and payment of the necessary fee.

DETAILED DESCRIPTION OF THE INVENTION

Figure 1:
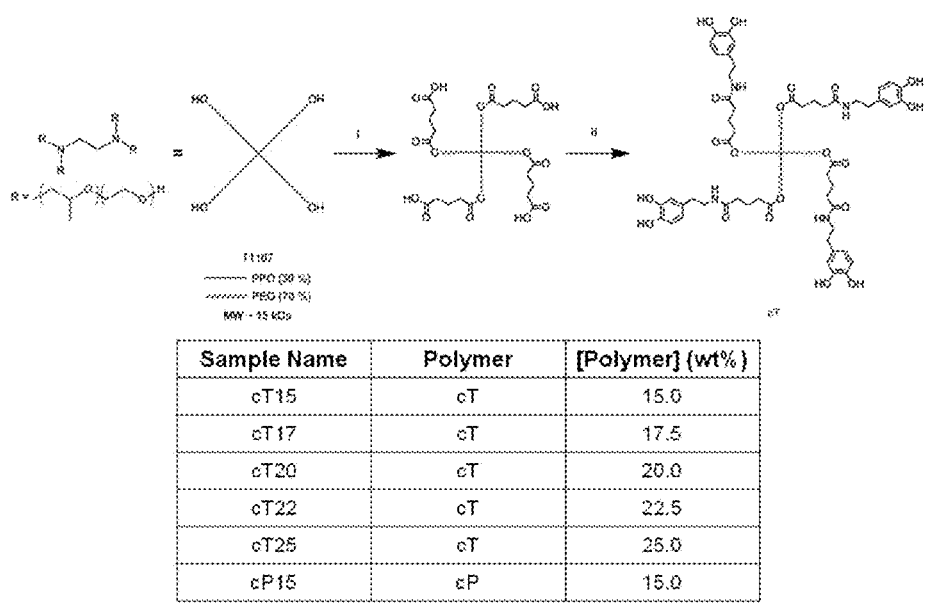
FIG. 1. Synthesis of catechol-modified Tetronic® (cT) and composition of hydrogels investigated in this study. (i) glutaric anhydride, pyridine; (ii) dopamine, HBTU, TEA. In all gels, the catechol-to-$IO_4^-$ ratio was 2:1.

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or—"an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The present invention provides mechanically tough zero- or negative-swelling mussel-inspired surgical adhesives based on catechol-modified amphiphilic poly(propylene oxide)-poly(ethylene oxide) block copolymers. The formation, swelling, bulk mechanical, and tissue adhesive properties of the resulting thermosensitive gels are characterized. Catechol oxidation at or below room temperature rapidly resulted in a chemically cross-linked network, with subsequent warming to physiological temperature inducing a thermal hydrophobic transition in the PPO domains and providing a mechanism for volumetric reduction and mechanical toughening. The described approach can be easily adapted for other thermally sensitive block copolymers and cross-linking strategies, representing a general approach that can be employed to control swelling and enhance mechanical properties of polymer hydrogels used in a medical context.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description of the present invention is to be regarded as illustrative in nature and not restrictive.

The Invention.

We have recently investigated mussel-mimetic hydrogels based on catechol modified polymers,[25,45,46,53-55] with in vitro, in vivo, and ex vivo studies demonstrating significant potential for use as medical adhesives and sealants.[26,46-48] The choice to use catechol-based chemistry is motivated by our discovery that marine mussels, which can attach to virtually any surface (organic or inorganic), use protein-based glues that contain 3,4-dihydroxy-L-phenylalanine (DOPA), a catechol-containing amino acid.[56,57] The most impressive aspect of these biological adhesives is that they are able to successfully function in aqueous environments that often cause the failure of other glues.[58,59] DOPA is particularly abundant at the interface between the adhesive foot pad and the substrate,[60-62] an observation that has resulted in significant speculation about the role of DOPA in the adhesive bonding of mussels.

Additionally, oxidized DOPA residues and DOPA-DOPA oligomers are thought to play important cohesive roles in the cross-linking reactions that lead to solidification of secreted adhesive precursors.[63,64] Our approach to designing medical adhesives, though significantly more simplistic than the natural mussel adhesive proteins, takes advantage of both the cohesive and adhesive capabilities of catechols. Oxidative cross-linking by $IO_4^-$ has been used in the past to form gels from catechol polymers by oxidizing catechols to reactive o-quinones that are capable of covalent coupling with catechols, amines, thiols, imidazoles, etc.

PEO has been employed as a polymer building block for approved medical sealants and a number of experimental formulations due to its long history of use in approved medical sealants, other medical devices, and pharmaceutical formulations.[5,46,65,66] However, most experimental and commercially available PEO-based hydrogels experience extensive swelling and suffer from mechanical weakness in the swollen state.[23,24,26]

Figure 13:
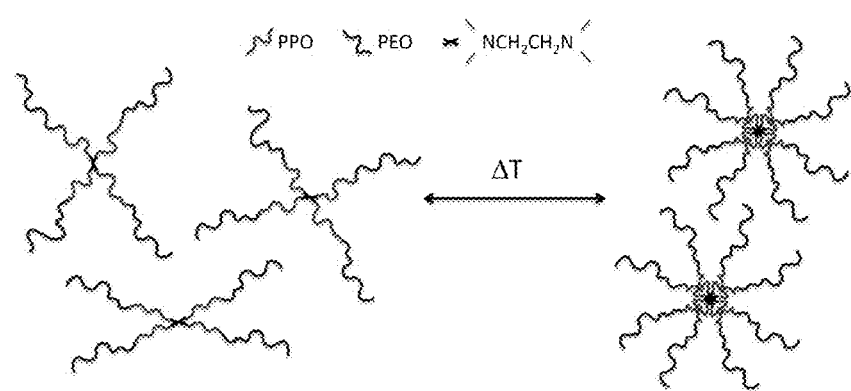
FIG. 13. Schematic illustration of the thermal transition of Tetronic® PPO-PEO block copolymers. Micelle-like aggregates form above the transition temperature as a result of hydrophobic collapse of PPO segments.

As these characteristics can lead to significant medical complications,[28-30] we aimed to circumvent these shortcomings by designing a zero- or negative-swelling, mechanically robust medical adhesive. More specifically, we sought to exploit the thermal transition associated with hydrophobic PPO blocks in PPO-PEO copolymers to induce gel contraction as a means to modulate the mechanical and swelling behavior. PPO is known to undergo a thermally induced transition from hydrophilic to hydrophobic in aqueous systems,[67,68] leading to a collapse of PPO into hydrophobic domains at modest temperatures (FIG. 13).

In the case of linear PPO-PEO block copolymers (Pluronic®), thermally induced micelle formation occurs in water-based solutions in order to minimize exposure of hydrophobic segments to water.[69-71] In highly concentrated solutions, the thermal transition induces physical gelation.[70,71] Tetronic® polymers, on the other hand, have four linear PPO-PEO arms emanating from a tetrafunctional ethylenediamine core (FIG. 1). Concentrated aqueous solutions of Tetronic® also undergo physical gelation at temperatures in the 20-35° C. range due to the hydrophobic transition associated with the PPO segments.[31-34] A number of studies have previously reported chemically cross-linked Tetronic® gels prepared by polymerization of terminal reactive functional groups.[31,36-44]

In their ground-breaking work, Tirelli and coworkers have reported a 'tandem' method of gelling thermosensitive polymers that combines both thermal and chemical gelation.[42,43] The tandem method, first described for Pluronic® polymers[42] and later for Tetronic®[43] as a mild means of cell encapsulation, relies on rapid thermal gelation of highly concentrated polymer solutions followed by chemical polymerization. Tandem cross-linked Pluronic® gels exhibited thermosensitive (LCST) properties and swelled >200% in pure water, though less in PBS.[42] Highly concentrated solutions of Tetronic® (30 wt %) thermally gel at ~20-21° C., allowing tandem formation of Tetronic® gels by rapid thermal gelation followed by slower chemical cross-linking.[43] Tandemly processed Tetronic® gels have been recently explored as tissue sealants, exhibiting decreased swelling and modest increases in tissue adhesion compared to PEO-based counterparts.[44] However, negative swelling gels were not reported. Catechol-modified linear PPO-PEO copolymers have also been explored by our lab in the past, but not in the context of negative swelling adhesives.[72]

Figure 7:
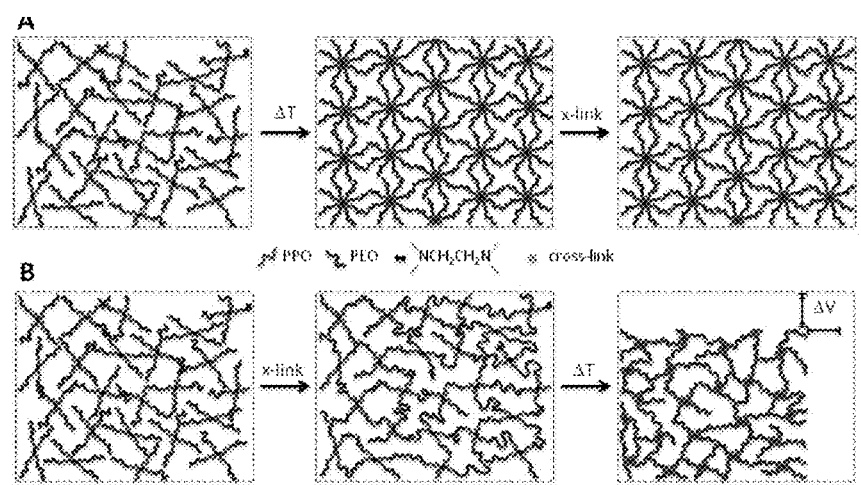
FIG. 7. Schematic illustration of chemically cross-linked PPO-PEO block copolymer thermoresponsive gels (not drawn to scale), demonstrating the significance of controlling the sequence of thermal transition and chemical cross-linking. (A) In the 'tandem' method of Cellesi et al.,[42,43] chemical cross-linking occurs after thermal equilibration. (B) In the present method, chemical cross-linking of cT is intended to occur prior to thermal equilibration, producing a PPO-PEO block copolymer network. Subsequent warming induces thermal transition of the PPO segments from hydrophilic to hydrophobic, producing volumetric shrinkage and toughening of the network.

We hypothesized that a negative-swelling thermosensitive polymer adhesive could be realized by avoiding widespread thermal gelation before chemical cross-linking through careful management of polymer composition and concentration, chemical cross-linking rate, and temperature. Thus, borrowing the terminology of Tirelli and coworkers, we employed an inverse 'tandem' method (FIG. 7).

Our method acknowledges a few key practical aspects associated with medical adhesive/sealant deployment in the clinic. First, we recognized that most medical sealants and adhesives are deployed at room temperature and are desired to solidify rapidly—instantaneously, a few seconds, or, at most, tens of seconds—upon contact with tissue. Secondly, the temperature of tissue surfaces during many clinical procedures is variable and can be significantly less than core body temperature, introducing an element of uncertainty with respect to methods requiring an increase in temperature for solidification of the adhesive.

Taking these practical aspects of medical adhesion into consideration, we sought to develop a system wherein rapid cross-linking chemistry coupled with subsequent thermal transition would give rise to negative swelling and enhanced mechanical properties. The oxidative mussel-mimetic catechol cross-linking chemistry met the desired cross-linking requirement due to the rapid rate of cross-linking upon mixing catechol polymers with a chemical oxidant.[45] The PPO block in Tetronic® provides the thermosensitivity due to a hydrophilic-to-hydrophobic transition with increasing temperature, as evidenced by a decrease of more than four orders of magnitude in critical micellization concentration (CMC) in the temperature range of 15-40° C.[73] Xu et al. has shown that a PPO core block of 33 repeat units undergoes self-association into micelles at 25° C.[74]

In our case, the PPO block length is shorter (~19 repeat units), giving rise to a moderately higher thermal transition. This facilitates the progression of chemical cross-linking prior to thermal equilibration to body temperature. Once chemical cross-linking gives rise to integration of hydrophilic PPO segments into the network, thermal self-association of PPO into hydrophobic domains is expected to result in negative swelling due to hydrophobic collapse (FIG. 7). Additionally, we surmised that collapsed hydrophobic PPO domains present in the network at elevated temperatures could act as energy dissipating domains that deform under applied load, leading to enhanced toughness (FIG. 14).[75-77]

Synthesis of catechol-modified PPO-PEO block copolymer (cT) proceeded in a facile manner from commercial Tetronic® 1107 using a glutarate linker, HBTU activation, and dopamine (FIG. 1). Gelation of a cT solution by $IO_4^-$ was rapid, as the cross-over point of G' and G" was not visible in the time sweeps of cT samples. Further rheological analysis of these hydrogels revealed unique, temperature-dependent behavior. For example, cT gels stiffened significantly upon heating from 20 to 40° C. (FIG. 2), a result that is consistent with thermomechanical behavior of chemically cross-linked Tetronic® gels[39] and with the formation of hydrophobic PPO domains within the same temperature range.[73,74] It is notable that G" increased dramatically over this temperature range, indicative of energy dissipation arising from hydrophobic PPO domains.

Figure 3:
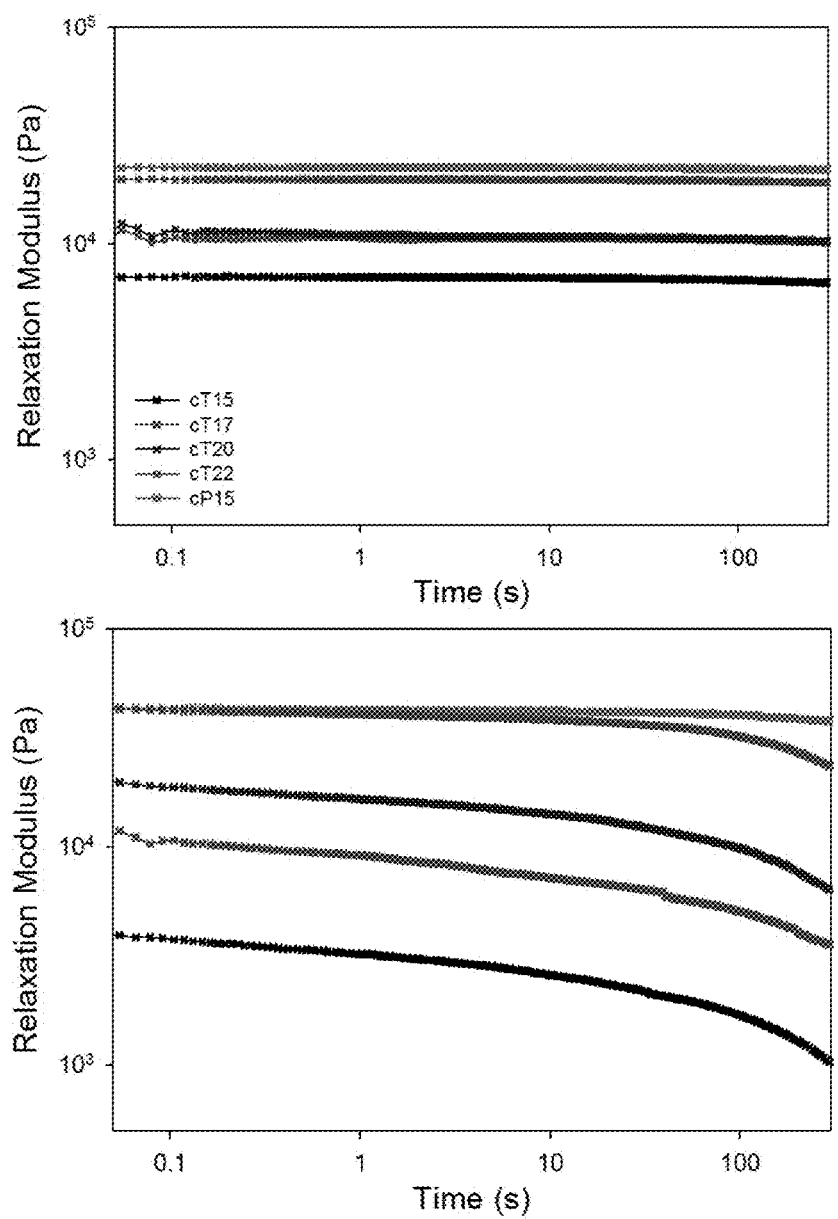
FIG. 3. Step-strain relaxation experiments showing the decay of modulus with time for cT and cP gels at 20° C. (top) and 40° C. (bottom). The legend applies to both the top and bottom panels.
Figure 9:
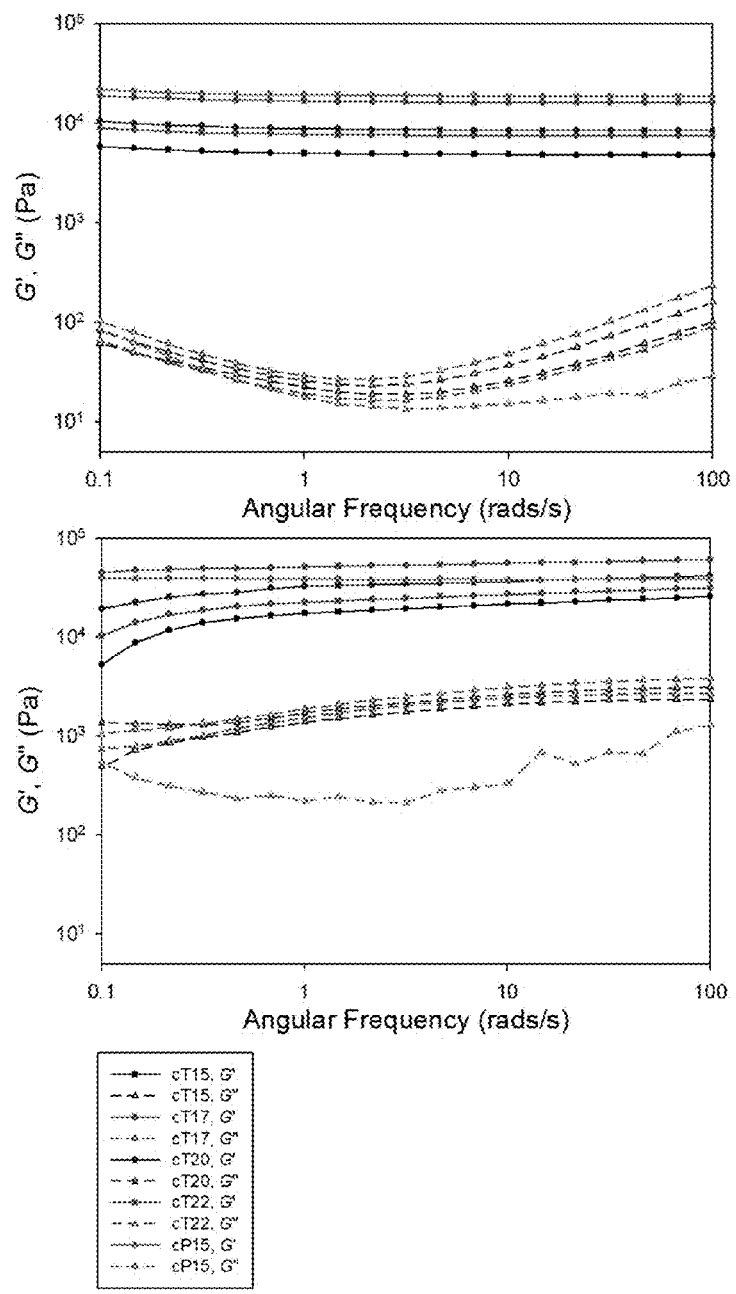
FIG. 9. Frequency dependence of storage (G') and loss (G") moduli of cT and cP hydrogels at 20° C. (top) and 40° C. (bottom).

Frequency sweep and step-strain experiments conducted at 20 and 40° C. revealed additional thermoresponsive behavior (FIG. 3 and FIG. 9). At room temperature, cT gels exhibited frequency-independent behavior, consistent with a covalently cross-linked network and similar to an identically cross-linked cP gel composed of PEO. However, cT gels show frequency-dependent moduli and significant relaxation when heated to 40° C. Such behavior was not observed in the PEO-based cP gels. This was most apparent in the step-strain relaxation experiments, in which the gel was exposed to a constant strain while changes in the storage modulus (here, called relaxation modulus) are monitored with time. cP gel modulus exhibited minimal relaxation (~13%) in this experiment, whereas cT gel moduli relaxed up to 74% in a concentration-dependent manner. We hypothesize that the temperature-dependent viscous behavior of cT hydrogels is based on the thermosensitive solubility of PPO in aqueous conditions.[67,68]

Figure 4:
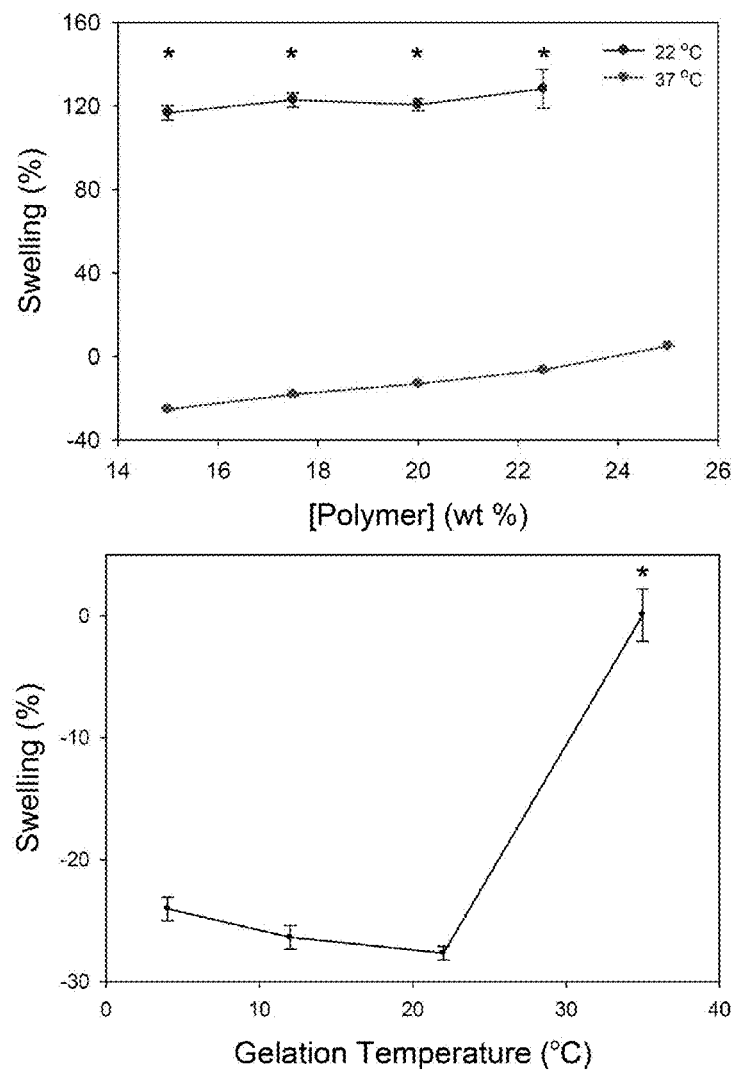
FIG. 4. Swelling of cT gels as a function of polymer concentration (top) and gel formation temperature (bottom). cT15 was studied in the temperature-based experiments (bottom panel). * indicates statistical significance ($p<0.001$) between 22 and 37° C. (top) and between samples cross-linked at 37° C. and all other temperatures (bottom).

The thermosensitivity of cT gels, and the contrasting behavior in comparison with PEO-based gels, was also apparent in swelling tests. It was interesting to note that, at room temperature, cP15 swelled much less than all cT gels over a 7-d study (FIG. 4, Tables 1 and 2).

TABLE 1

Swelling of cT and cP hydrogels at 22° C.

| Material | Temperature (° C.) | Time (d) | Swelling (%) |
|---|---|---|---|
| cT15 | 22 | 1 | 123.7 ± 4.0 |
|  |  | 2 | 129.0 ± 4.4 |
|  |  | 3 | 126.5 ± 4.4 |
|  |  | 7 | 116.7 ± 3.4 |
| cT17 | 22 | 1 | 125.0 ± 6.5 |
|  |  | 2 | 131.9 ± 3.9 |
|  |  | 3 | 130.1 ± 3.5 |
|  |  | 7 | 122.9 ± 3.4 |

TABLE 1-continued

Swelling of cT and cP hydrogels at 22° C.

| Material | Temperature (° C.) | Time (d) | Swelling (%) |
|---|---|---|---|
| cT20 | 22 | 1 | 115.9 ± 6.2 |
|  |  | 2 | 124.2 ± 5.5 |
|  |  | 3 | 123.9 ± 4.1 |
|  |  | 7 | 120.6 ± 2.9 |
| cT22 | 22 | 1 | 120.0 ± 14.3 |
|  |  | 2 | 130.6 ± 10.6 |
|  |  | 3 | 129.2 ± 10.5 |
|  |  | 7 | 128.3 ± 9.3 |
| cP15 | 22 | 1 | 79.1 ± 9.7 |
|  |  | 2 | 80.7 ± 10.8 |
|  |  | 3 | 81.8 ± 5.4 |
|  |  | 7 | 73.6 ± 5.5 |

TABLE 2

Swelling of cT and cP hydrogels at 37° C.

| Material | Temperature (° C.) | Time (d) | Swelling (%) |
|---|---|---|---|
| cT15 | 37 | 1 | −22.4 ± 0.5 |
|  |  | 2 | −24.3 ± 0.5 |
|  |  | 3 | −24.7 ± 0.4 |
|  |  | 7 | −25.3 ± 0.5 |
| cT17 | 37 | 1 | −16.4 ± 1.1 |
|  |  | 2 | −17.7 ± 1.0 |
|  |  | 3 | −17.9 ± 1.0 |
|  |  | 7 | −18.1 ± 0.9 |
| cT20 | 37 | 1 | −12.0 ± 0.6 |
|  |  | 2 | −12.9 ± 0.3 |
|  |  | 3 | −13.1 ± 0.5 |
|  |  | 7 | −13.1 ± 0.4 |
| cT22 | 37 | 1 | −6.0 ± 0.4 |
|  |  | 2 | −6.4 ± 0.4 |
|  |  | 3 | −6.6 ± 0.5 |
|  |  | 7 | −6.5 ± 0.5 |
| cT25 | 37 | 1 | 4.7 ± 0.5 |
|  |  | 2 | 4.7 ± 0.2 |
|  |  | 3 | 3.9 ± 0.3 |
|  |  | 7 | 5.0 ± 0.1 |
| cP15 | 37 | 1 | 58.6 ± 4.2 |
|  |  | 2 | 50.7 ± 5.0 |
|  |  | 3 | 50.9 ± 2.2 |
|  |  | 7 | 49.5 ± 7.7 |

We believe that this observation can be explained by the fact that each arm in the cT precursor is ~50% larger by weight relative to cP and that PPO segments retained hydrophilic character at room temperature. Therefore, if we assume that the cross-linking reaction proceeds to an equivalent conversion in both cases, the cT gels would have a larger molecular weight between cross-links, explaining the higher swelling at room temperature. When swelling studies were conducted at 37° C., both cT and cP gels displayed a reduction in the extent of swelling, presumably due to the LCST of PEO[49,50] and PPO-PEO.[69-71] At 37° C., cP15 swelled ~50%, whereas cT contracted 7-25% in a concentration-dependent manner (FIG. 4).

Previous reports of gels designed from covalently linked 4-arm PPO-PEO copolymers describe various levels of swelling and contraction at 37° C.[36,43,44] We believe the origin of these disparities to be related to differences in the PPO aggregation state at the time of cross-linking, arising from differences in relative rates of chemical gelation versus thermal gelation/micellization. Supporting this hypothesis, a second set of swelling tests involved forming cT gels at 4, 12, 22, or 35° C. for 18 h and then measuring swelling at 37° C. after 24 h. Swelling was found to be greatly affected by the gelation temperature (FIG. 4). For cT gels formed at or below room temperature, in which PPO domains remain hydrophilic, negative swelling was observed at 37° C. This result is consistent with the notion that hydrophobic collapse of PPO domains induced by warming to 37° C. resulted in volumetric contraction by ~25%.

In contrast, using a method that is analogous to the 'tandem' gelation method (thermally induced gelation followed by chemical cross-linking), gels formed at 35° C. did not demonstrate negative swelling after 1 day at 37° C. This result is consistent with previous reports,[43,44] and can be understood as a consequence of the hydrophobic state of PPO prior to cross-linking; as no hydrophobic PPO collapse is accessible to induce network contraction, negative swelling should not occur.

Figure 2:
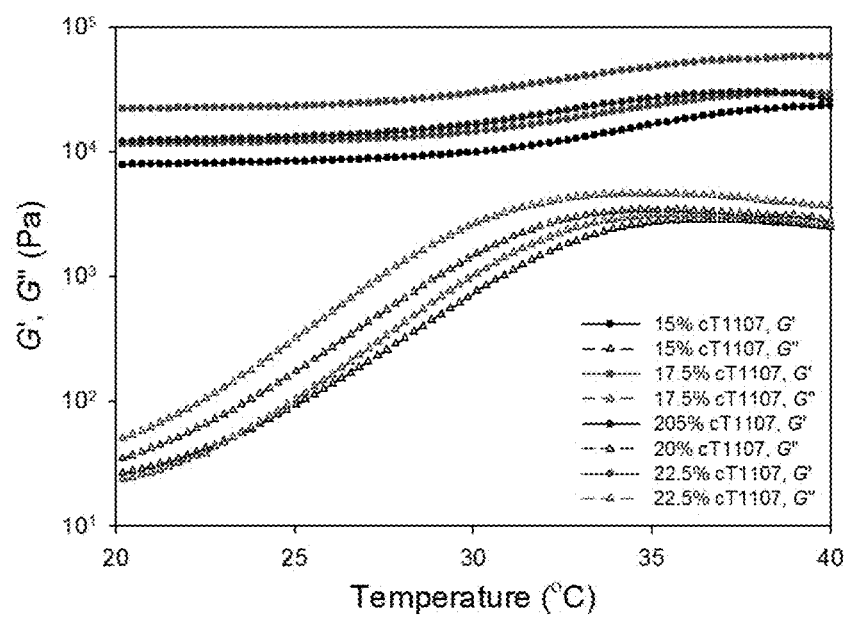
FIG. 2. Temperature dependence of the storage (G', closed symbols) and loss (G", open symbols) moduli of cT gels.

Previous investigations of the mechanical behavior of chemically cross-linked Tetronic® gels have been limited to rheological or macroscopic measurements of stiffness.[36,39,43] As expected, our rheological and bulk mechanical compression experiments revealed increases in modulus of cT gels when heated above room temperature (FIG. 2 and Table 3).

TABLE 3

Bulk Mechanical Properties of Adhesive cT Hydrogels.

| Sample Notes | Sample | Compressive Modulus (kPa) | Maximum Stress (MPa) | Strain at Failure (%) | Relative Energy Dissipated (%) |
|---|---|---|---|---|---|
| As-made and tested at 22° C. | cT15 | 28.2 ± 8.4 | 3.4 ± 0.9 | >90[a] | NC[b] |
|  | cT17 | 55.7 ± 3.6 | 4.3 ± 0.2 | >90[a] | NC[b] |
|  | cT20 | 63.6 ± 17.6 | 4.3 ± 0.2 | >90[a] | NC[b] |
|  | cT22 | 83.4 ± 10.0 | 4.2 ± 0.4 | >90[a] | NC[b] |
|  | cP15 | 99.0 ± 9.7 | 1.0 ± 0.6 | 76.1 ± 2.8 | NC[b] |
| Equilibrated for 24 h and tested in 37° C. PBS | cT15 | 92.2 ± 13.2 | 1.0 ± 0.02 | >90[a] | 38.2 ± 0.6 |
|  | cT17 | 116.9 ± 10.9 | 1.0 ± 0.04 | >90[a] | 34.0 ± 4.2 |
|  | cT20 | 165.1 ± 41.3 | 1.3 ± 0.05 | >90[a] | 29.3 ± 4.0 |
|  | cT22 | 195.4 ± 32.6 | 1.3 ± 0.1 | >90[a] | 37.2 ± 4.9 |
|  | cP15 | 114.7 ± 10.8 | 0.8 ± 0.1 | 82.5 ± 3.1 | NA[c] |

[a]cT samples did not fail when compressed to 90% strain;

[b]not calculated;

[c]Energy dissipation calculations could not be performed for cP samples because failure occurred before unloading curve was observed.

This stiffening was realized without sacrificing extensibility, as all cT hydrogels survived 90% compression and maximum stresses of ~1 MPa; in contrast, cP gels failed at lower maximum strain and stress.

Figure 5:
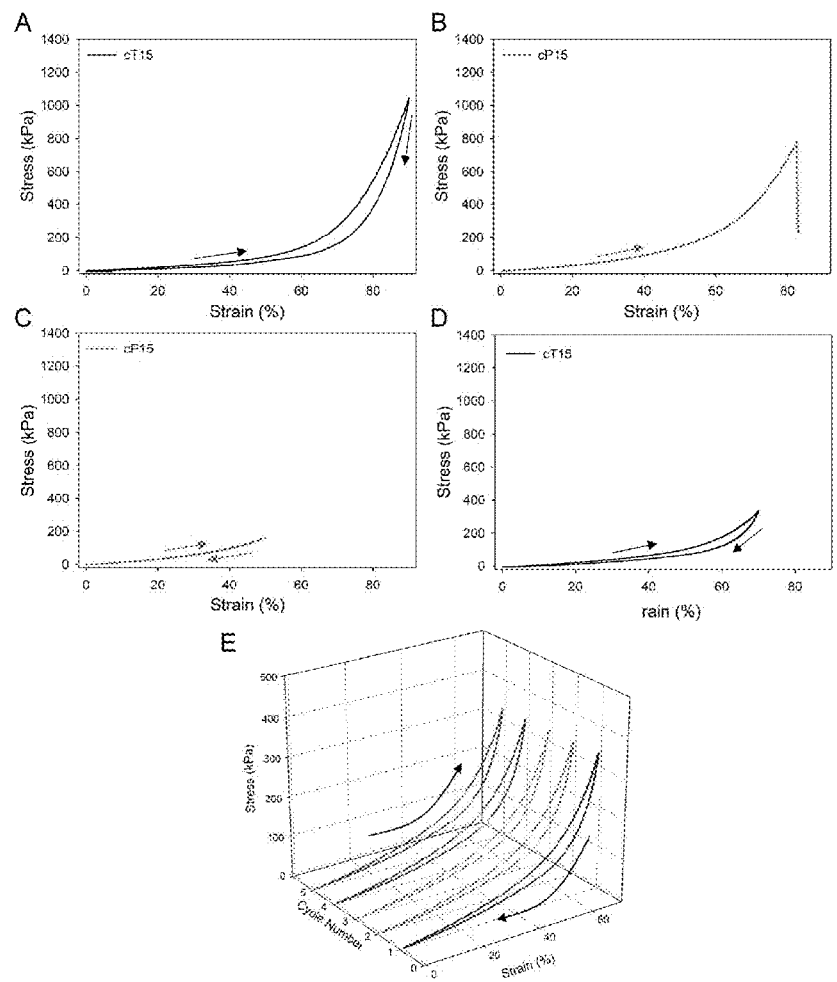
FIG. 5. Bulk compression of 15% gels at 37° C. Gels were equilibrated at physiological temperature for 24 h and then loaded in compression up to 90% strain at constant temperature. The loading and unloading portion of the curves are identified with arrows. (A) cT15 gels survived 90% strain without rupture, while (B) cP15 gels ruptured at ~80% strain. (C) Compression loading of cP15 to 50% followed by unloading revealed no hysteresis between loading and unloading portions of the curve. (D, E) Gels were repeatedly loaded in compression up to 70% strain at constant temperature. Successive compression cycles are shown superimposed (D) and separated (E).
Figure 11:
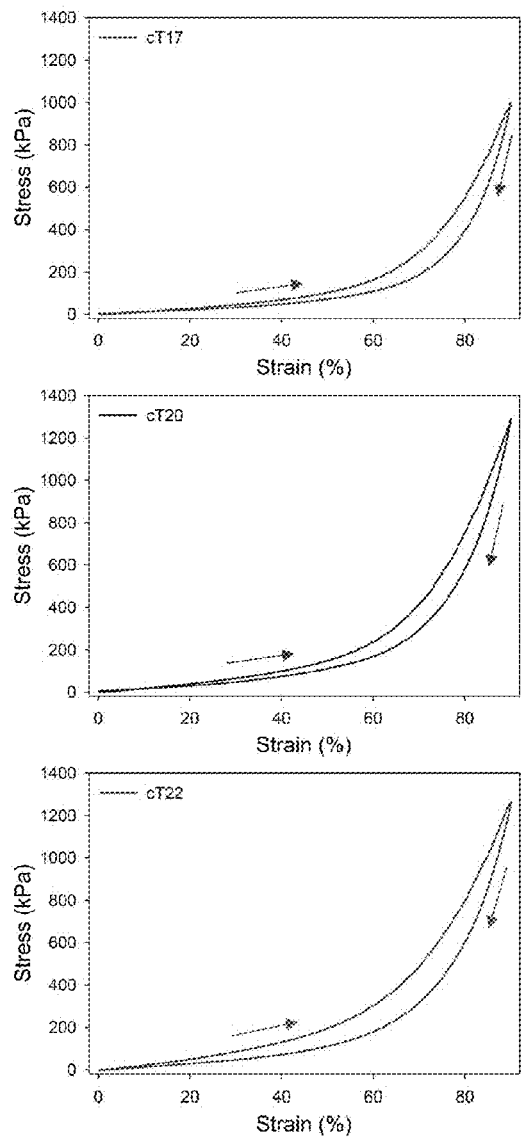
FIG. 11. Bulk compression of cT gels at 37° C. cT17 (top), cT20 (middle), and cT22 (top) were equilibrated at physiological temperature for 24 h and then loaded in compression up to 90% strain at constant temperature. The loading and unloading portion of the curves are identified with arrows. All cT gels survived 90% strain without rupture.
Figure 12:
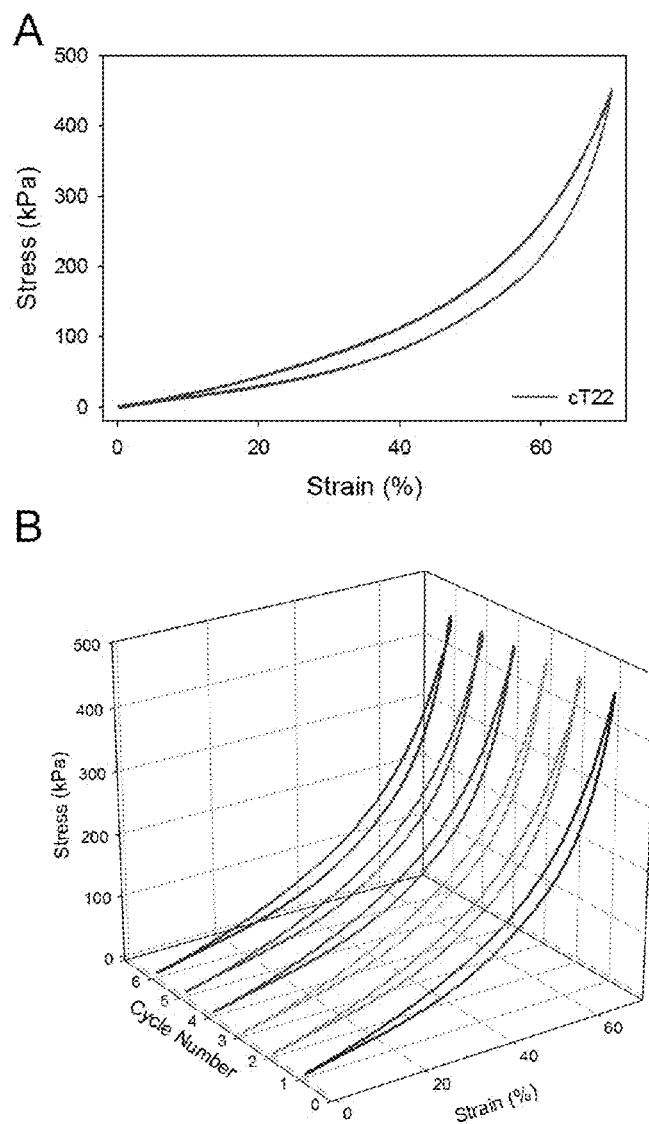
FIG. 12. Cyclic fatigue testing of cT22. Gels were equilibrated at 37° C. for 24 h and then repeatedly loaded in compression up to 70% strain at constant temperature. Six compression cycles are shown superimposed (A) or separated (B).
Figure 14:
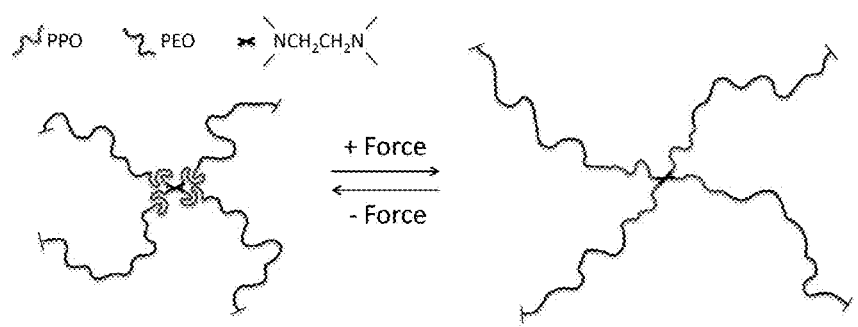
FIG. 14. Schematic illustration of the molecular behavior of cT gels under mechanical loading. A possible explanation for the observed mechanical hysteresis involves energy-dissipating mechanical extension of the collapsed hydrophobic PPO domains when the covalently linked network is strained, revealing hidden length exposed by force-induced elongation of polymer chains.

However, the existence of significant relaxation of cT gels at 40° C. (FIG. 3) has not been previously reported and suggested more complicated mechanical behavior, perhaps involving viscous energy dissipation mechanisms connected to the presence of hydrophobic PPO domains present within the gel network. Indeed, significant mechanical hysteresis was observed at 37° C. in the bulk compression curves of cT gels, but not in cP gels (FIG. 5, FIG. 11). We hypothesize that this behavior is at least partially caused by the presence of hydrophobic domains in cT gels, whose formation is driven by the thermally induced collapse of PPO segments. A possible explanation for the mechanical hysteresis involves disruption of the hydrophobic domains when the covalently linked cT network is strained, revealing hidden length[78] by force-induced elongation of polymer chains (FIG. 14). Similar behavior is a key feature of several biological tissues, such as tendon and cartilage, where the viscoelastic response of these tissues is very important in energy dissipation and load transfer.[79-82] Stress-strain plots of cT gel samples subjected to several successive loading and unloading cycles perfectly overlapped (FIG. 5, FIG. 12), indicating a high level of robustness and resistance to damage under extreme loading conditions.

Figure 6:
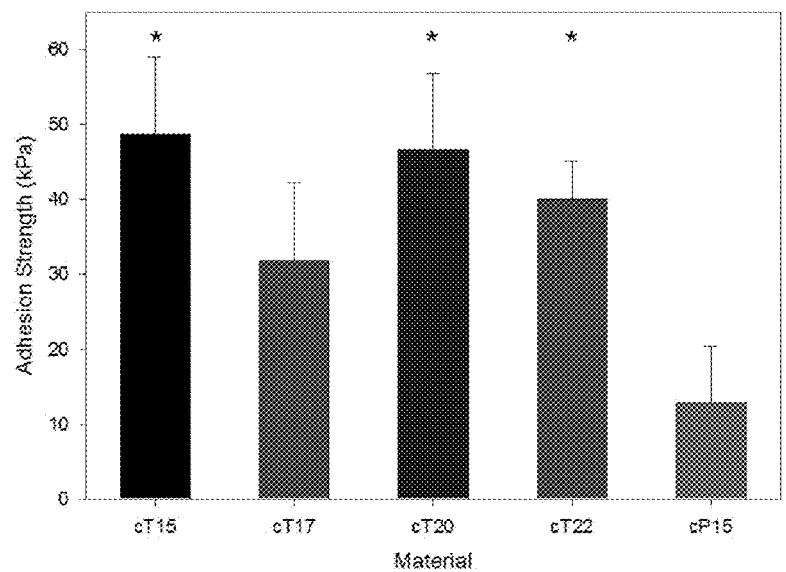
FIG. 6. Comparison of lap shear tissue adhesion performance. Samples were immersed in 1×PBS for 1 h at 37° C. and then tested wet. * represents statistical significance ($p<0.05$) relative to cP15.

Finally, the performance of cT and cP gels as tissue adhesives was investigated (FIG. 6). In order to probe adhesive performance shortly after application, tissue samples were bonded together using either cT or cP gels and allowed to cure at 37° C. for 1 h while fully submerged in PBS; this method is in contrast to protocols that call for longer (2-24 h) cross-linking periods and/or minimally hydrated environments.[25,44,52] Although we found no clear trends of lap shear strength with respect to cT concentration, all cT gel concentrations tested (15-22.5 wt %) outperformed cP samples. cT gels exhibited adhesion strengths of 31-49 kPa, 2.5-4 times greater than that of cP15 (12.7 kPa). Interestingly, one of the strongest adhesives (cT15) also exhibited the greatest degree of contraction (negative swelling), suggesting that negative swelling does not compromise adhesion strength.

Although our highest lap shear adhesive strength (49 kPa) is well above the mean value recently reported by Cho et al. for a chemically cross-linked Tetronic® adhesive formed by the tandem method,[44] comparisons must be approached with caution due to the use of different test methodologies, cross-linking chemistries and tissues. Our own experiences have led us to believe that key parameters affecting results include the method of incubation during the curing period and the swelling state of the adhesive (equilibrium or nonequilibrium). To illustrate this, we can make some comparisons with other catechol-modified PEO adhesive systems from our lab due to their structural similarity to cP and utilization of the same cross-linking chemistry involving catechol oxidation.[25,52]

Previously, we achieved adhesion strengths of cP-like gels in the range of 30-35 kPa for gels incubated in a humid atmosphere;[25,52] in the present study, we incubated cP-bonded tissue samples in PBS at 37° C. during the 1-h curing period and achieved an adhesion strength of only ~13 kPa. Although the gels are unlikely to achieve equilibrium (negative) swelling within 1 h even with full immersion in PBS, the current results nevertheless suggest that the adhesion strength of PEO-based materials is significantly weakened by swelling in an aqueous environment. In contrast, the adhesion strength of cT gel remained high under full immersion conditions, implying that the mechanical strength of cT gels may be retained under equilibrium swelling conditions.

We have described the synthesis and characterization of mussel-inspired hydrogel adhesives that combine biologically inspired covalent adhesive chemistry with a thermally sensitive block copolymer. The resulting polymer gels possess covalent catechol-catechol cross-links between branched PPO-PEO block copolymers. This network is augmented by thermosensitive transitions of PPO blocks, which exhibit a hydrophobic collapse upon heating to physiological temperature.

Chemical cross-linking using rapid catechol oxidation chemistry at or below room temperature followed by warming to body temperature, resulted in hydrophobic collapse of PPO domains and contraction of the gel. Through variation of polymer concentration and gel formation temperature, swelling could be systematically controlled in the range of zero to −25%. Rheological experiments showed that the gel stiffened above the PPO thermal transition. Strength and toughness of the gels was greater than those of analogous PEO-based gels, with PPO-PEO block copolymer gels surviving 90% compression and exhibiting significant mechanical hysteresis between loading and unloading curves.

Finally, the tissue adhesive potential was demonstrated through lap shear adhesion measurements of decellularized porcine dermis, producing bond strengths greater than PEO-based adhesives. This novel class of thermosensitive biomaterials represents a facile and versatile synthetic route to strong hydrogels, enhancing the adhesion strength of mussel-inspired polymer hydrogels.

The following example, is, of course, offered for illustrative purposes only, and is not intended to limit the scope of the present invention in any way. Indeed, various modifications of the invention in addition to those shown and described herein will become apparent to those skilled in the art from the foregoing description and the following examples and fall within the scope of the appended claims.

Example 1

Materials:

Tetronic® 1107 (T1107, MW≈15 kDa; 30 wt % PPO, 70 wt % PEO) was a generous gift from BASF (Florham Park, N.J.). PEO (4-arm, MW≈10 kDa) was purchased from JenKem Technology USA, Inc. (Allen, Tex.). 2-(1H-benzotriazole-1-yl)-1,1,3,3-tetramethyluronium hexafluorophosphate (HBTU) was purchased from Chem-Impex International (Wood Dale, Ill.). Sodium meta-periodate ($NaIO_4$) and glutaric anhydride (GA) were purchased from Sigma-Aldrich (Milwaukee, Wis.). Dopamine hydrochloride (DA), triethylamine (TEA), 4-nitrophenyl chloroformate (4NPC), dichloromethane (DCM), dimethylformamide (DMF), tetrahydrofuran (THF), and methanol (MeOH) were purchased from Fisher Scientific (Philadelphia, Pa.). All chemicals were used without further purification. Dehydrated and decellularized porcine dermis was a gift from Kensey Nash Corporation (Exton, Pa.).

Synthesis of Catechol-Tetronic® (cT):

T1107 (10 g) and glutaric anhydride (5× mol. equiv. relative to —OH) were added to a two-neck round-bottom flask, which was then purged with Ar. Anhydrous chloroform (70 mL) and THF (20 mL) were added. The solids were stirred until fully dissolved. Pyridine (5× mol. equiv. relative to —OH) was added, and the reaction was refluxed under Ar for ~18 h. The reaction solution was then washed with brine and water, dried with MgSO$_4$, filtered, and concentrated under reduced pressure. The glutarate-modified T1107 intermediate was precipitated in ether and dried under vacuum overnight.

Purified glutarate-modified T1107 was dissolved in DCM (50 mL) and DMF (50 mL). DA (1.2× mol. equiv. relative to —COOH) was added and completely dissolved. HBTU (1.2× mol. equiv. relative to —COOH) was added and completely dissolved. TEA (2.5× mol. equiv. relative to —COOH) was added, and the reaction was stirred for 1.5 h before being concentrated under reduced pressure. The polymer was precipitated in acidified ether, dried under vacuum overnight, and dissolved in ~100 mL of 12.1 mM HCl. The solution was filtered, dialyzed (3500 MWCO) against water at pH 4 for 24 h, dialyzed against MilliQ water for 4 h, frozen at −80° C., and lyophilized. The final cT polymer was obtained as a white solid and stored under Ar at −20° C. until needed.

Synthesis of Catechol-PEO (cP):

cP was synthesized by adding 10 g PEO to a two-neck round-bottom flask, which was purged with Ar. Anhydrous DCM (80 mL) was added to dissolve the PEO. TEA (2.5× mol. equiv. relative to —OH) was added, and the solution was stirred for 15 min. Separately, 4NPC (2.5× mol. equiv. relative to —OH) was dissolved in anhydrous DCM (20 mL) and slowly added to the PEO solution. The reaction was allowed to proceed for ~18 h at room temperature in an inert environment of Ar. The volume was reduced by rotary evaporation, and the activated PEO (4PEO-NPC) was collected by precipitation in cold ether and −20° C. MeOH (2×). The product was then dried under vacuum overnight.

Purified 4PEO-NPC was combined with 90 mL of a 2:1 (v/v) solution of DMF and DCM. Once dissolved, DA (2.5× mol. equiv. relative to —NPC) was added. When the solution was homogeneous, the reaction was activated by the addition of TEA (2.5× mol. equiv. relative to —NPC) and stirred for ~18 h. The volume was reduced by rotary evaporation, and the PEO was collected by precipitation in acidified cold ether and acidified MeOH at −20° C. The product was then dried under vacuum overnight and dissolved in ~100 mL of 12.1 mM HCl. The solution was filtered, dialyzed (3500 MWCO) against water at pH 4 for 24 h, dialyzed against MilliQ water for 4 h, frozen at −80° C., and lyophilized. The final purified cP was obtained as a white solid and stored under Ar at −20° C. until needed.

Hydrogel Formation:

Solutions of cT in 2×PBS and NaIO$_4$ in water (7/1 v/v) were mixed at room temperature such that the final polymer concentration was 150, 175, 200, or 225 mg/mL and the catechol:IO$_4^-$ was 2:1 (FIG. 1). Hydrogels of cP were formed by combining equal volumes of 300 mg/mL cP in 2×PBS and 12 mg/mL NaIO$_4$ in water at room temperature.

Rheometry:

Rheological characterization was performed on an Anton Paar MCR 300 rheometer with a CP 25-2 fixture (25 mm diameter, 2° cone angle), peltier hood, and an evaporation shield. Solutions of IO$_4^-$ and either cT or cP were mixed as above (except that cP was dissolved in 2×PBS at pH 7.0) and added as a liquid onto the rheometer baseplate. The fixture was brought down into contact with the liquid mixture as quickly as possible. For all samples, the following tests were performed in sequence: time test (20 Pa shear stress, 10 rads/s, 20° C.), frequency sweep (5% strain, 100 rads/s to 0.1 rads/s, 20° C.), relaxation experiment (10% strain, 20° C., stress monitored for ~300 s), temperature sweep (5% strain, 10 rads/s, 20° C. to 40° C., 1° C./min), frequency sweep (5% strain, 100 rads/s to 0.1 rads/s, 40° C.), relaxation experiment (10% strain, 40° C., stress monitored for ~300 s).

Swelling of Hydrogels:

Two sets of swelling experiments were conducted on pre-formed gels. In the first method, gels were formed as described above by introducing liquid precursor mixture into a polytetrafluoroethylene mold and allowing the gel to solidify for 15 minutes at room temperature. Gel samples were removed from the molds, weighed and immersed in 1×PBS at room temperature or 37° C. for 1, 2, 3, or 7 d. At specified time points, samples were removed from PBS, blotted to remove excess surface water, and weighed.

In the second set of swelling experiments, precursor solutions for cT15 samples were equilibrated for 30 min at either 4, 12, 22, or 35° C. Gels were then formed as described above by introducing liquid precursor mixtures into a polytetrafluoroethylene mold. Gels were allowed to solidify for 18 h at the same temperatures used to equilibrate precursor solutions. Gel samples were then removed from the molds, weighed, and immersed in 1×PBS at 37° C. After 1 d, samples were removed from PBS, blotted to remove excess surface water, and weighed.

Swelling (Q) was calculated by $$Q = \frac{m_f - m_i}{m_i} \times 100 \quad (1)$$

where $m_f$ and $m_i$ represent the initial and final mass of the hydrogels, respectively. Three replicates were performed and the average value was reported.

Bulk Compression Testing of Adhesive Hydrogels:

Compression tests were conducted on a Sintech 20/G mechanical tester equipped with a 1000-lb load cell. Gels were formed as described above by introducing liquid precursors into a polytetrafluoroethylene mold and allowing the gel to solidify for 15 minutes at room temperature. Gel samples were removed from the molds and tested in the unswollen state or after swelling for 24 h at 37° C. Samples were strained to 90% at a crosshead speed of 10 mm/min at room temperature in air or 37° C. in 1×PBS. Compressive moduli were calculated by determining the slope of the first 5% of the stress-strain curve. Ultimate compressive stress (UCS) and failure strain were defined as the largest stress and strain values recorded before samples failed. The areas under the curve (AUC) for both loading and unloading portions of the curve were estimated by the rectangle method in MATLAB.

Energy dissipation was calculated by $$\text{Energy Dissipation} = \frac{AUC_L - AUC_U}{AUC_L} \times 100 \quad (2)$$

where $AUC_L$ and $AUC_U$ represent the areas under the loading and unloading curves, respectively. Three trials were performed and the average value was reported.

Lap-Shear Testing:

The performance of cT hydrogels as tissue adhesives was analyzed in a lap shear test based on ASTM standard F2255-05[27] Dehydrated and decellularized porcine dermis was reconstituted for >1 h in 1×PBS and cut to size (2.5 cm×2.0 cm). Tissue substrates were glued onto aluminum fixtures using cyanoacrylate glue (Permabond 268, Permabond, Pottstown, Pa.) and cured for 1 h at 37° C., keeping the fixture wrapped in PBS-soaked gauze to prevent dehydration of the tissue. The gel precursors were mixed as described above and 100 µL of the adhesive solution was applied to the tissue surface. A second tissue sample on an aluminum fixture was immediately brought into contact with the adhesive, achieving an overlapping (adhesive bonded) area of approximately 2.5 cm×1.0 cm. A 100-g weight was placed on the fixture assembly for ~15 min, after which test samples were submerged for 1 h in 1×PBS at 37° C. Immediately prior to tensile testing, samples were removed from the water bath, and the area of substrate overlap was measured using digital calipers. Samples were strained until failure in lap shear on a Sintech 20/G mechanical tester equipped with a 1000-lb load cell at 37° C. with a cross-head speed of 5 mm/min.

Statistical Analysis:

Statistical significance was conducted with IBM SPSS Statistics software by a one-way analysis of variance (ANOVA) with a Bonferroni post-hoc test.

Results.

Oscillatory Rheometry.

Figure 8:
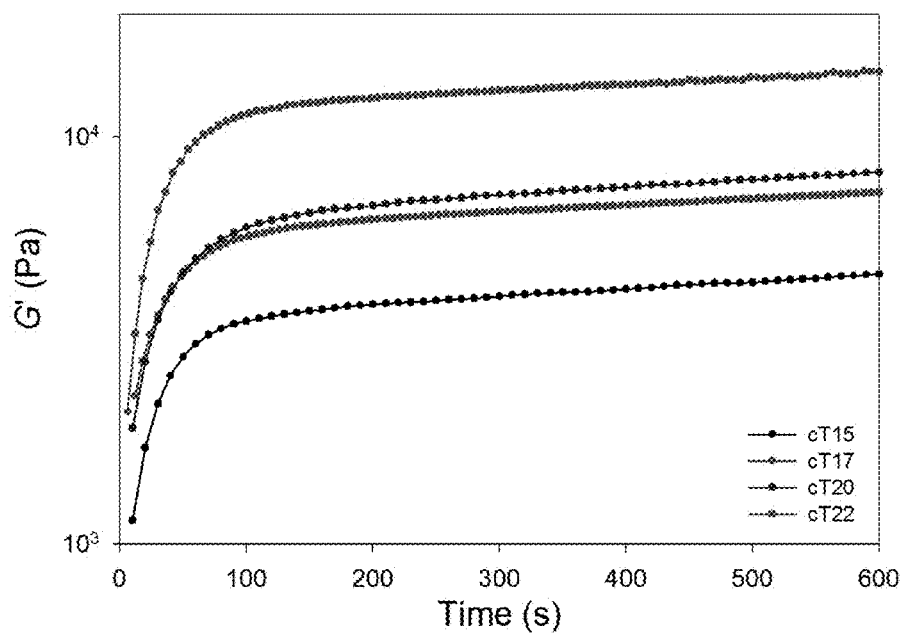
FIG. 8. Time sweep showing the storage (G') modulus of cT1107 gels during cross-linking at 20° C.

Solutions of cT in 2×PBS and NaIO$_4$ in water (7/1 v/v) were mixed to induce cross-linking (catechol:IO$_4^-$ of 2:1) and added to the rheometer. Gels with final cT concentrations of 150, 175, 200, or 225 mg/mL are designated cT15, cT17, cT20, and cT22, respectively (FIG. 1). Covalent cT gels were then studied by rheology as a function of polymer content and temperature. Periodate-induced gelation occurred quickly (<30 s) at 20° C. in all cases, as evidenced by the fact that we were unable to record the cross-over point between the storage (G') and loss (G") moduli. The storage modulus increased rapidly in the first several minutes of reaction and approached a plateau within ten minutes, with the value of the plateau modulus increasing with cT concentration (FIG. 8). The thermosensitive behavior of cT gels was analyzed by forming gels in situ within the rheometer at 20° C., followed by monitoring G' and G" during a temperature sweep from 20-40° C. (FIG. 2). G' of cT gels increased approximately 2.5-fold between 30 and 37° C., and G" displayed a dramatic (~100-fold) increase over a wider temperature range (20-35° C.).

Considering the increase in G" as evidence of viscous effects at high temperature, we next probed the frequency-dependent behavior using frequency sweep and step-strain (relaxation) experiments. As seen in FIG. 9, cT gels probed at 20° C. appear to behave as elastic solids as judged by their frequency-independent behavior with G'>>G". Step-strain experiments, in which the decay of modulus was monitored at constant strain (10%), revealed little stress relaxation in cT hydrogels at 20° C. (FIG. 3). This property was shared by a control gel composed of PEG (cP15) and is consistent with covalently cross-linked elastic networks.

Frequency sweeps of cT gels conducted at 40° C. revealed only slight frequency-dependent behavior at high angular frequency (>1 rads/s). However, a viscous response became increasingly apparent at very low angular frequencies (<0.3 rads/s) (FIG. 9), though G' was greater than G" at all angular frequencies tested. The relaxation behavior of cT gels was more evident in step-strain experiments conducted at 40° C. (FIG. 3), in which the relaxation moduli of cT15, cT17, cT20, and cT22 gels decayed to 26, 30, 32, and 55% of initial value within 5 min, respectively. This behavior was in stark contrast to cP15 cross-linked in an identical manner, which displayed minimal decrease in relaxation modulus at 40° C. (~13%) over the same amount of time.

Gel Swelling.

Swelling of cT samples was studied in 1×PBS at 22° C. and 37° C. (FIG. 4, Table 1-2) for up to 7 days. In almost all cases, equilibrium was reached after 1 day. At 22° C., cT gels swelled between 110% and 140% over a 7-d study, which is considerably greater than the swelling of cP15 (50-60%). At 37° C., cT hydrogels exhibited concentration-dependent negative swelling (contraction) (FIG. 4). After 7 d at 37° C., cT15, cT17, cT20, cT22, and CT25 showed swelling values of approximately −25, −18, −13, −7, and +4%, respectively. A fit of the plot of cT concentration as a function of swelling at 37° C. was highly linear ($r^2$≈0.98), providing a guideline for tailoring gel swelling/contraction behavior through cT concentration. In contrast, cP gels swelled 30-50% at physiological temperature. Equilibrium swelling of cP gels was lower at 37° C. than at room temperature, which we attribute to the proximity of our experimental conditions (37° C., high ionic strength) to the lower critical solution temperature (LCST) of PEO.[49,50]

A second swelling test probed the influence of gelation temperature on 37° C. swelling of cT15 gels. Precursor solutions were equilibrated to 4, 12, 22, or 35° C. before mixing, and were cured at the same temperature for 18 h. After being removed from molds, cT15 samples were swelled for 24 h in PBS at 37° C. Samples that were cross-linked at 4, 12, or 22° C. swelled approximately −25% (FIG. 4). However, gels that were equilibrated and cured at 35° C. displayed no swelling or contraction.

Compression Testing.

The bulk mechanical properties of cT gels were studied by loading hydrogel cylinders in compression up to 90% strain (the compression limit of our equipment), followed by unloading. Both loading and unloading data were recorded, and elastic moduli were estimated from the initial portion of the loading curves (<5% strain). At room temperature and in the unswollen state, cP15 gel had a compression modulus of 99 kPa, whereas cT gels had moduli in the range of 28-83 kPa (Table 3). All unswollen cT gels were superior to cP gels in terms of extensibility and strength; cT gels survived compressive stresses of 3.4-4.3 MPa and 90% strain without damage, whereas cP15 gels failed at 76% strain and 1.0 MPa UCS.

Figure 10:
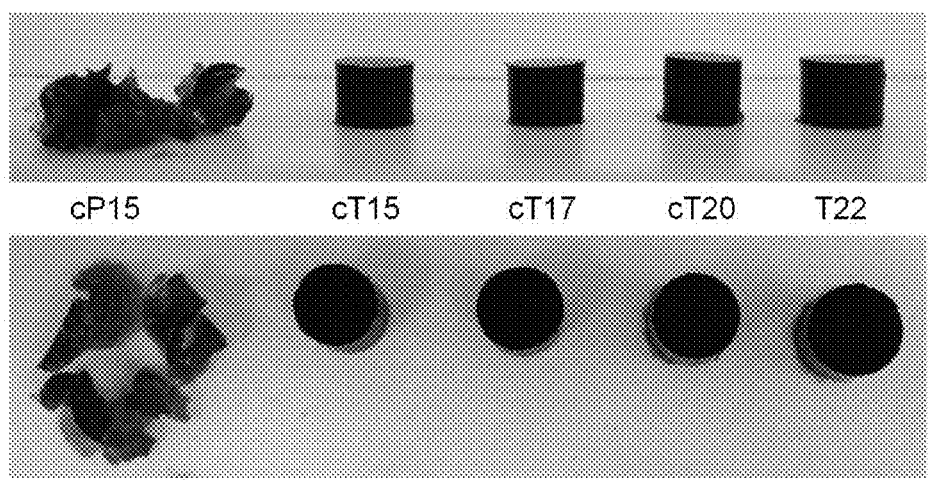
FIG. 10. Photographs of hydrogel cylinders after testing to 90% bulk compression at 37° C. cT gels were undamaged whereas cP15 gel was fractured.

At physiological temperature in the swollen state (24 h in PBS), the compression moduli of cT gels increased with cT concentration, ranging from 92, 117, 165, and 195 kPa for cT15, cT17, cT20, and cT22, respectively. These values were substantially higher than the same samples at 22° C. in the unswollen state (Table 1). cT hydrogels were able to withstand 90% compression at 37° C. in the equilibrium swollen state (FIG. 10), though the maximum stresses at 90% strain (~1 MPa) were significantly less than at room temperature (~3-4 MPa). In contrast, the mechanical behavior of cP15 at 37° C. in the swollen state (modulus of 115 kPa, 0.8 MPa UCS, 83% strain at failure) was not significantly different compared to the unswollen state at 22° C.

For cT gels in particular, a notable feature of the bulk mechanical behavior was the presence of significant hysteresis between the loading and unloading portions of the stress-strain curves (FIG. 5, FIG. 11). Hysteresis was particularly evident in the highly nonlinear region from 50-90% strain. AUC differences between the loading and unloading curves provided a measure of energy dissipation during deformation,[51] which was found to be in the range 23-29%. Stress-strain curves of cT gel samples subjected to multiple loading/unloading cycles in succession nearly perfectly overlapped (FIG. 5, FIG. 12), providing further evidence of the lack of damage induced by severe compression loading of cT gels.

Tissue Adhesion.

The ability of cT hydrogel to mechanically adhere hydrated tissue surfaces together was studied via lap shear testing with decellularized porcine dermis. Samples of cT15, cT17, cT20, and cT22, cured for 1 h in PBS at 37° C., demonstrated lap shear adhesive strengths of 48.7, 31.9, 46.6, and 40.0 kPa, respectively (FIG. 6). Adhesives of cP15 were also tested, yielding a lap shear adhesion strength of ~13 kPa, which is significantly less than previously studied formulation based on catechol-modified PEO.[25,52]

In summary, we have described mechanically tough zero- or negative-swelling mussel-inspired surgical adhesives based on catechol-modified amphiphilic poly(propylene oxide)-poly(ethylene oxide) block copolymers. The formation, swelling, bulk mechanical, and tissue adhesive properties of the resulting thermosensitive gels are characterized. Catechol oxidation at or below room temperature rapidly resulted in a chemically cross-linked network, with subsequent warming to physiological temperature inducing a thermal hydrophobic transition in the PPO domains and providing a mechanism for volumetric reduction and mechanical toughening. The described approach can be easily adapted for other thermally sensitive block copolymers and cross-linking strategies, representing a general approach that can be employed to control swelling and enhance mechanical properties of polymer hydrogels used in a medical context.

The above description and figures attached hereto (and incorporated by reference herein) are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

[1] H. K. Kjaergard. *Am J Surg* 2001, 182, 515.
[2] H. Lau. *Am Surg* 2005, 242, 670.
[3] R. Schwab; A. Willms; A. Kröger; H. Becker. *Hernia* 2006, 10, 272.
[4] M. Ryou; C. C. Thompson. *Tech Gastrointest Endosc* 2006, 8, 33.
[5] H. T. Peng; P. N. Shek. *Expert Rev Med Dev* 2010, 7, 639.
[6] H. Seyednejad; N. Imani; T. Jamieson; A. M. Seifalian. *Brit J Surg* 2008, 95, 1197.
[7] M. R. Jackson. *Am J Surg* 2001, 182, 51.
[8] C. Joch. *Cardiovacs Surg* 2003, 11, 23.
[9] P. J. Klimo et al. *Neurosurgery* 2007, 60, 305.
[10] P. A. Leggat; D. R. Smith; U. Kedjarune. *ANZ J Surg* 2007, 77, 209.
[11] G. J. Mattamal. *Expert Rev Med Dev* 2008, 5, 41.
[12] H. E. Achneck et al. *Ann Surg* 2010, 251, 217.
[13] M. Glickman; A. Gheissari; S. Money; J. Martin; J. L. Ballard. *Arch Surg* 2002, 137, 326.
[14] C. P. Napoleone et al. *Interact Cardiovasc Thorac Surg* 2009, 9, 978.
[15] W. R. Ranger et al. *Am Surg* 1997, 63, 788.
[16] M. S. Allen et al. *Ann Thorac Surg* 2004, 77, 1792.
[17] G. R. Cosgrove et al. *J Neurosurg* 2007, 106, 52.
[18] K. D. Than; C. J. Baird; A. Olivi. *Neurosurgery* 2008, 63, 182.
[19] E. L. Park et al. *J Urol* 2004, 172, 2446.
[20] R. Ufret et al. *Invest Ophthalmol Vis Sci* 2004, 45, U767.
[21] S. W. Kim; Y. H. Bae; T. Okano. *Pharm Res* 1992, 9, 283.
[22] N. A. Peppas; J. Z. Hilt; A. Khademhosseini; R. Langer. *Adv Mater* 2006, 18, 1345.
[23] P. K. Campbell Evaluation of Absorbable Surgical Sealants: In Vitro Testing; In: *In Vitro Testing*; Edited by S. L. Bennett, A. Driscoll, A. S. Sawhney; Covidien Laboratories: Mansfield, Mass., 2007.
[24] A. N. Azadani et al. *Ann Thorac Surg* 2009, 87, 1154.
[25] C. E. Brubaker; P. B. Messersmith. *Biomacromolecules* 2011, 12, 4326.
[26] M. Mehdizadeh; H. Weng; D. Gyawali; L. Tang; J. Yang. *Biomaterials* 2012, 33, 7972.
[27] ASTM F2255-05 (2010), "Standard Test Method for Strength Properties of Tissue Adhesives in Lap-Shear by Tension Loading," ASTM International, West Conshohocken, Pa., 2010, DOI: 10.1520/F2255-05R10, www.astm.org.
[28] S. L. Blackburn; M. D. Smyth. *J Neurosurg: Pediatr* 2007, 106, 302.
[29] M. Mulder; J. Crosier; R. Dunn. *Spine* 2009, 34, E144.
[30] D. Thavarajah; P. De Lacy; R. Hussain; R. M. Redfern. *Spine* 2010, 35, E25.
[31] S. Garty et al. *Biomacromolecules* 2010, 11, 1516.
[32] D. H. Go et al. *Macromol Biosci* 2008, 8, 1152.
[33] C. Alvarez-Lorenzo; et al. *Euro J Pharm Biopharm* 2007, 66, 244.
[34] D. A. Chiappetta et al. *Nanomedicine NBM* 2011, 7, 624.
[35] Z. You; H. Cao; J. Gao; P. H. Shin; B. W. Day; Y. Wang. *Biomaterials* 2010, 31, 3129.
[36] A. Sosnik; M. V. Sefton. *J Biomed Mater Res A* 2005, 75A, 295.
[37] A. Sosnik; R. N. S. Sodhi; P. M. Brodersen; M. V. Sefton. *Biomaterials* 2006, 27, 2340.
[38] K. M. Park; Y. K. Joung; K. D. Park. *Tissue Eng A* 2008, 14, 849.
[39] K. M. Park et al. *Biomacromolecules* 2010, 11, 706.
[40] K. M. Park; I. Jun; Y. K. Joung; H. Shin; K. D. Park. *Soft Matter* 2011, 7, 986.
[41] K. M. Park et al. *Biomacromolecules* 2012, 13, 604.
[42] F. Cellesi; N. Tirelli; J. A. Hubbell. *Macromol Chem Phys* 2002, 203, 1466.
[43] F. Cellesi; N. Tirelli; J. A. Hubbell. *Biomaterials* 2004, 25, 5115.
[44] E. Cho; J. S. Lee; K. Webb. *Acta Biomater* 2012, 8, 2223.
[45] B. P. Lee; J. L. Dalsin; P. B. Messersmith. *Biomacromolecules* 2002, 3, 1038.
[46] C. E. Brubaker et al. *Biomaterials* 2010, 31, 420.
[47] G. Bilic et al. *Am J Obstet Gynecol* 2010, 202, 85.e1.
[48] C. M. Haller et al. *Prenatal Diagn* 2011, 31, 654.
[49] S. Saeki; N. Kuwahara; M. Nakata; M. Kaneko. *Polymer* 1976, 17, 685.
[50] R. Kjellander; E. Florin. *J Chem Soc, Faraday Trans 1* 1981, 77, 2053.
[51] S. Lv; D. M. Dudek; Y. Cao; M. M. Balamurali; J. Gosline; H. Li. *Nature* 2010, 465, 69.

[52] S. A. Burke; M. Ritter-Jones; B. P. Lee; P. B. Messersmith. *Biomed Mater* 2007, 2, 203.
[53] Y. Lee et al. *Soft Matter* 2010, 6, 977.
[54] J. H. Ryu et al. *Biomacromolecules* 2011, 12, 2653.
[55] N. Holten-Andersen et al. *Proc Natl Acad Sci USA* 2011, 108, 2651.
[56] J. H. Waite. *J Biol Chem* 1983, 258, 2911.
[57] B. P. Lee et al. *Ann Rev Mater Res* 2011, 41, 99.
[58] J. H. Waite. *Int J Adhes Adhes* 1987, 7, 9.
[59] T. H. Anderson et al. *Adv Funct Mater* 2010, 20, 4196.
[60] J. H. Waite; M. L. Tanzer. *Science* 1981, 212, 1038.
[61] V. V. Papov; T. V. Diamond; K. Biemann; J. H. Waite. *J Biol Chem* 1995, 270, 20183.
[62] J. H. Waite; X. X. Qin. *Biochemistry* 2001, 40, 2887.
[63] M. E. Yu; J. Y. Hwang; T. J. Deming. *J Am Chem Soc* 1999, 121, 5825.
[64] L. A. Burzio; J. H. Waite. *Biochemistry* 2000, 39, 11147.
[65] N. Artzi et al. *Macromol Biosci* 2009, 9, 754.
[66] I. Strehin; Z. Nahas; K. Arora; T. Nguyen; J. Elisseeff. *Biomaterials* 2010, 31, 2788.
[67] G. N. Malcolm; J. S. Rowlinson. *Trans Faraday Soc* 1957, 53, 921.
[68] L. S. Sandell; D. A. I. Goring. *J Polym Sci A-2* 1971, 9, 115.
[69] I. Schmolka. *J Am Oil Chem Soc* 1977, 54, 110.
[70] P. Alexandridis; J. F. Holzwarth; T. A. Hatton. *Macromolecules* 1994, 27, 2414.
[71] P. Alexandridis; T. Alan Hatton. *Colloids Surf A* 1995, 96, 1.
[72] K. Huang; B. P. Lee; D. R. Ingram; P. B. Messersmith. *Biomacromolecules* 2002, 3, 397.
[73] G. Wanka; H. Hoffmann; W. Ulbricht. *Macromolecules* 1994, 27, 4145.
[74] J. Xu; Z. Ge; Z. Zhu; S. Luo; H. Liu; S. Liu. *Macromolecules* 2006, 39, 8178.
[75] S. Abdurrahmanoglu; V. Can; O. Okay. *Polymer* 2009, 50, 5449.
[76] A. Matsuda; T. Kaneko; J. Gong; Y. Osada. *Macromolecules* 2000, 33, 2535.
[77] C. Zhang; A. Aung; L. Liao; S. Varghese. *Soft Matter* 2009, 5, 3831.
[78] G. E. Fantner et al. *Biophys J* 2006, 90, 1411.
[79] D. C. Taylor; J. D. Dalton; A. V. Seaber; W. E. Garrett. *Am J Sports Med* 1990, 18, 300.
[80] G. A. Johnson et al.; N.-Y. Choi; S. L-Y. Woo. *J Orthopaed Res* 1994, 12, 796.
[81] W. C. Hayes; L. F. Mockros. *J Appl Physiol* 1971, 31, 562.
[82] A. F. Mak. *J Biomech Eng* 1986, 108, 123.

We claim:

1. A method for making a non-swelling medical adhesive comprising a hydrogel in a PBS solution at physiological temperature, the method comprising:
   (a) contacting a composition comprising a catechol-modified poly(ethylene oxide)-poly(propylene oxide) block copolymer having four linear PPO-PEO arms emanating from a tetrafunctional ethylenediamine core with a biocompatible oxidant in a PBS solution at room temperature or below, whereby the catechol-modified poly(ethylene oxide)-poly(propylene oxide) block copolymer is chemically cross-linked to form a hydrogel;
   (b) increasing the temperature of the resulting hydrogel in the PBS solution to physiological temperature; and
   (c) thermally equilibrating the hydrogel at physiological temperature, whereby the hydrogen exhibits no or negative swelling after at least one day in PBS solution at 37° C.

2. The method of claim 1, wherein room temperature is about 20° C. or about 22° C.

3. The method of claim 1, wherein physiological temperature is about 37° C.

4. The method of claim 1, wherein one or more terminal ends of the catechol-modified poly(ethylene oxide)-poly(propylene oxide) block copolymer includes a catechol moiety.

5. The method of claim 4, wherein the catechol-modified poly(ethylene oxide)-poly(propylene oxide) block copolymer has the structure A(B—C)$_4$,
wherein A is,

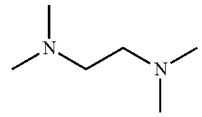

B is

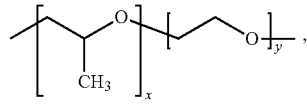

wherein x is about 19 and y is about 59; and,
C is a catechol-terminating moiety.

6. The method of claim 5, wherein C is

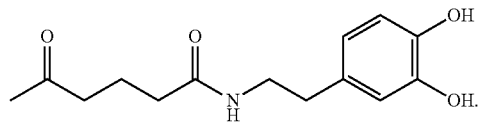 [SMILES: CC(=O)CCCC(=O)NCCc1ccc(O)c(O)c1]

7. The method of claim 1, wherein the oxidant is a periodate.

8. The method of claim 7, wherein the periodate is sodium periodate.

9. The method of claim 7, wherein the mole ratio of catechol present in the catechol-modified poly(ethylene oxide)-poly(propylene oxide) block copolymer to the periodate oxidant is 2:1.

10. A non-swelling medical adhesive in a PBS solution at 37° C. made by the method of claim 1, wherein the poly(propylene oxide) block within the catechol-modified poly(ethylene oxide)-poly(propylene oxide) block copolymer that is chemically cross-linked to form the hydrogel comprises a hydrophobic domain.

11. A non-swelling medical adhesive comprising a hydrogel in a PBS solution at physiological temperature made by mixing a solution of two or more catechol-modified poly(ethylene oxide)-poly(propylene oxide) block copolymer molecules having four linear PPO-PEO arms emanating from a tetrafunctional ethylenediamine core with a biocompatible oxidant in a PBS solution at room temperature or below for at least fifteen minutes, whereby the catechol-modified poly(ethylene oxide)-poly(propylene oxide) block copolymers are chemically cross-linked to each other between the catechol moieties of adjacent block copolymer molecules, and increasing the temperature of the resulting hydrogel in the PBS solution to equilibrate the hydrogen to physiological temperature for at least one day wherein the hydrogel exhibits no or negative swelling while being exposed to a PBS solution at 37° C. after temperature equilibration.

12. The medical adhesive of claim 11, wherein one or more terminal ends of the block copolymer molecules include a catechol moiety.

13. The medical adhesive of claim 12, wherein the catechol-modified poly(ethylene oxide)-poly(propylene oxide) block copolymer molecules have the structure A(B—C)$_4$,
wherein A is

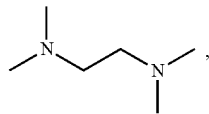

B is

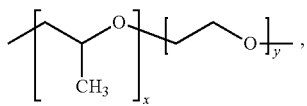

wherein x is about 19 and y is about 59; and
C is a catechol-terminating moiety.

14. The medical adhesive of claim 13, wherein C is

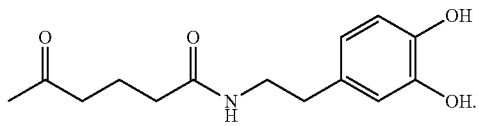 [SMILES: CC(=O)CCCC(=O)NCCc1ccc(O)c(O)c1]

15. The method of claim 1, wherein the catechol-modified poly(ethylene oxide)-poly(propylene oxide) block copolymer comprises about 70% by weight of poly(polypropylene oxide) and about 30% weight of poly(ethylene oxide).

16. The non-swelling medical adhesive of claim 10, wherein the catechol-modified poly(ethylene oxide)-poly(propylene oxide) block copolymer comprises about 70% by weight of poly(polypropylene oxide) and about 30% weight of poly(ethylene oxide).

17. The non-swelling medical adhesive of claim 11, wherein the catechol-modified poly(ethylene oxide)-poly(propylene oxide) block copolymer comprises about 70% by weight of poly(polypropylene oxide) and about 30% weight of poly(ethylene oxide).

18. The non-swelling medical adhesive of claim 10, wherein the adhesive exhibits an adhesion strength of about 31-49 kPa.

* * * * *